(12) United States Patent (10) Patent No.: US 8,829,208 B2
Mizhiritskii et al. (45) Date of Patent: Sep. 9, 2014

(54) PROCESS FOR THE PREPARATION OF DARUNAVIR AND DARUNAVIR INTERMEDIATES

(75) Inventors: Michael Mizhiritskii, Rehovot (IL); Ehud Marom, Kfar Saba (IL)

(73) Assignee: Mapi Pharma Ltd., Ness Ziona (IL)

( * ) Notice: Subject to any disclaimer, the term of this patent is extended or adjusted under 35 U.S.C. 154(b) by 46 days.

(21) Appl. No.: 13/519,297

(22) PCT Filed: Jan. 24, 2011

(86) PCT No.: PCT/IL2011/000079
§ 371 (c)(1),
(2), (4) Date: Jun. 26, 2012

(87) PCT Pub. No.: WO2011/092687
PCT Pub. Date: Aug. 4, 2011

(65) Prior Publication Data
US 2012/0296101 A1 Nov. 22, 2012

Related U.S. Application Data
(60) Provisional application No. 61/298,941, filed on Jan. 28, 2010.

(30) Foreign Application Priority Data
Jul. 1, 2010 (WO) .................. PCT/IL2010/000533

(51) Int. Cl.
*C07D 493/04* (2006.01)
(52) U.S. Cl.
CPC .................................... *C07D 493/04* (2013.01)
USPC ........................................................ 549/464
(58) Field of Classification Search
CPC .................................................... C07D 493/04
USPC ........................................................ 549/464
See application file for complete search history.

(56) References Cited

U.S. PATENT DOCUMENTS

| | | | |
|---|---|---|---|
| 4,415,747 A | 11/1983 | Kaplan | |
| 5,744,481 A | 4/1998 | Vazquez et al. | |
| 5,786,483 A | 7/1998 | Vazquez et al. | |
| 5,830,897 A | 11/1998 | Vazquez et al. | |
| 5,843,946 A | 12/1998 | Vazquez | |
| 5,968,942 A | 10/1999 | Vazquez | |
| 6,037,157 A | 3/2000 | Norbeck | |
| 6,046,190 A | 4/2000 | Vazquez et al. | |
| 6,060,476 A | 5/2000 | Vazquez et al. | |
| 6,172,082 B1 | 1/2001 | Vazquez et al. | |
| 6,248,775 B1 | 6/2001 | Vazquez | |
| 6,335,460 B1 | 1/2002 | Vazquez | |
| 6,417,387 B1 | 7/2002 | Vazquez et al. | |
| 6,455,581 B1 | 9/2002 | Vazquez et al. | |
| 6,472,407 B2 | 10/2002 | Vazquez et al. | |
| 6,500,832 B1 | 12/2002 | Vazquez et al. | |
| 6,534,493 B1 | 3/2003 | Vazquez et al. | |
| 6,613,743 B2 | 9/2003 | Hale | |
| 6,646,010 B2 | 11/2003 | Vazquez et al. | |
| 6,703,403 B2 | 3/2004 | Norbeck | |
| 6,846,954 B2 | 1/2005 | Vazquez et al. | |
| 6,852,887 B2 | 2/2005 | Malik | |
| 6,919,465 B2 | 7/2005 | Ghosh et al. | |
| 6,924,286 B1 | 8/2005 | Vazquez | |
| 7,115,618 B2 | 10/2006 | Vazquez | |
| 7,141,609 B2 | 11/2006 | Vazquez | |
| 7,320,983 B2 | 1/2008 | Vazquez | |
| 7,470,506 B1 | 12/2008 | Erickson | |
| 7,531,538 B2 | 5/2009 | Vazquez | |
| 7,700,645 B2 | 4/2010 | Vermeersch | |
| 2002/0026079 A1 | 2/2002 | Kronenthal et al. | |
| 2004/0127727 A1 | 7/2004 | Ghosh | |
| 2004/0162340 A1 | 8/2004 | Ikemoto | |
| 2005/0089164 A1 | 4/2005 | Lang | |
| 2005/0250845 A1 | 11/2005 | Vermeersch | |
| 2005/0256322 A1 | 11/2005 | Ikemoto | |
| 2006/0135562 A1 | 6/2006 | Kraft et al. | |
| 2006/0135563 A1 | 6/2006 | Kraft | |
| 2006/0148865 A1 | 7/2006 | Martin | |
| 2007/0060642 A1 | 3/2007 | Goyvaerts | |
| 2009/0131363 A1 | 5/2009 | Harbeson | |
| 2010/0168422 A1 | 7/2010 | Chen | |
| 2012/0035142 A1 | 2/2012 | Marom | |

FOREIGN PATENT DOCUMENTS

| | | |
|---|---|---|
| CA | 2485834 A1 | 12/2003 |
| CN | 1668623 A | 9/2005 |
| DE | 69332002 T2 | 12/2002 |
| EP | 0715618 A1 | 6/1996 |
| EP | 0754669 A1 | 1/1997 |
| EP | 0810209 A2 | 12/1997 |
| EP | 1029856 A1 | 8/2000 |
| EP | 1067125 A1 | 1/2001 |
| EP | 1081133 A1 | 3/2001 |
| EP | 1215209 A1 | 6/2002 |
| EP | 1661893 A2 | 5/2006 |
| EP | 1889826 A1 | 2/2008 |
| ES | 2123065 T3 | 1/1999 |
| ES | 2127938 T3 | 5/1999 |
| ES | 2177868 T3 | 12/2002 |

(Continued)

OTHER PUBLICATIONS

Brittain H.G. (1999) Polymorphism in Pharmaceutical Solids. CRC Press, New York City, pp. 184-226.

(Continued)

*Primary Examiner* — Taofiq A Solola
(74) *Attorney, Agent, or Firm* — Rothwell, Figg, Ernst & Manbeck, P.C.

(57) ABSTRACT

The present invention relates to a process for the preparation of darunavir, a nonpeptide protease inhibitor (PI), useful for the treatment of HIV/AIDS patients harboring multidrug-resistant HIV-1 variants that do not respond to previously existing HAART regimens. The present invention further relates to processes for the stereo-directed preparation of darunavir intermediates, in particular (3R,3aS,6aR)-hexahydrofuro[2,3-b]furan-3-ol and to certain novel intermediates obtained by such processes.

25 Claims, No Drawings

(56) References Cited

FOREIGN PATENT DOCUMENTS

| | | |
|---|---:|---|
| FI | 119427 B | 11/2008 |
| JP | 09124629 A | 5/1997 |
| WO | 94/04492 A1 | 3/1994 |
| WO | 95/06030 A1 | 3/1995 |
| WO | 99/67254 A2 | 12/1999 |
| WO | 99/67417 A2 | 12/1999 |
| WO | 03/022853 A1 | 3/2003 |
| WO | 03/024974 A2 | 3/2003 |
| WO | 03/060905 A1 | 7/2003 |
| WO | 03/106461 A2 | 12/2003 |
| WO | 2004/016619 A1 | 2/2004 |
| WO | 2004/033462 A2 | 4/2004 |
| WO | 2004/094465 A2 | 11/2004 |
| WO | 2005/000249 A2 | 1/2005 |
| WO | 2005/063770 A1 | 7/2005 |
| WO | 2005/087728 A1 | 9/2005 |
| WO | 2005/095410 A1 | 10/2005 |
| WO | 2005/110428 A2 | 11/2005 |
| WO | 2006/108879 A2 | 10/2006 |
| WO | 2006/132390 A1 | 12/2006 |
| WO | 2007/060253 A1 | 5/2007 |
| WO | 2007/126812 A2 | 11/2007 |
| WO | 2008/016522 A2 | 2/2008 |
| WO | 2008/034598 A1 | 3/2008 |
| WO | 2008/055970 A2 | 5/2008 |
| WO | 2008/132154 A1 | 11/2008 |
| WO | 2009/000853 A2 | 12/2008 |
| WO | 2009/005674 A2 | 1/2009 |
| WO | 2009/030733 A1 | 3/2009 |
| WO | 2009/081174 A2 | 7/2009 |
| WO | 2010/002998 A1 | 1/2010 |
| WO | 2010/023322 A1 | 3/2010 |
| WO | 2010/086844 A1 | 8/2010 |
| WO | 2011/048604 A2 | 4/2011 |
| WO | 2011/051978 A2 | 5/2011 |
| WO | 2011/073993 A1 | 6/2011 |
| WO | 2011/083287 A2 | 7/2011 |
| WO | 2011/092687 A1 | 8/2011 |
| WO | 2011/141921 A1 | 11/2011 |

OTHER PUBLICATIONS

Beaulieu, Pierre L et al., (1995) Large scale preparation of (2S,3S)-N-Boc-3-amino-1,2-epoxy-4-phenylbutane: A key building block for HIV-protease inhibitors Tetrahedron Letters, 1995, 36(19):3317-3320.

Bull, Steven D. et al.,(1998) Chiral relay auxiliaries. Pure & Appl. Chem. 70(8):1501-1506.

Cohen, Noal et al., (1983) Enantiospecific syntheses of leukotrienes C4, D4, and E4, and [14,15-3H2]leukotriene E4 dimethyl ester. J. Am. Chem. Soc. 105(11):3661-3672.

Contreras, Jordi and Jones, J. Idris (1980) Synthesis of Poly(p-Benzenesulphonamide) Part I. Preparation of Sulphanilic Acid Derivatives for Use as Intermediates. British Polymer Journal 12(4):192-198.

Ghosh, Arun K. et al., (1998) Potent HIV protease inhibitors incorporating high-affinity P2-ligands and (R)-(hydroxyethylamino)sulfonamide isostere. Bioorg Med Chem Lett 8(6):687-690.

Ghosh, Arun K. et al., (2004) Stereoselective Photochemical 1,3-Dioxolane Addition to 5-Alkoxymethyl-2(5H)-furanone: Synthesis of Bis-tetrahydrofuranyl Ligand for HIV Protease Inhibitor UIC-94017 (TMC-114) J. Org Chem. 69 (2004) 7822-7829.

Gioeli, Carlo and Chattopadhyaya, Jyoti B. (1982) The fluoren-9-ylmethoxycarbonyl group for the protection of hydroxy-groups; its application in the synthesis of an octathymidylic acid fragment. J Chem Soc, Chem commun 1982 (12):672-674.

Griffith, William P. et al, (1987) Preparation and use of tetra-n-butylammonium per-ruthenate (TBAP reagent) and tetra-n-propylammonium per-ruthenate (TPAP reagent) as new catalytic oxidants for alcohols. J. Chem. Soc. Chem Commun. 1987(21):1625-1627.

Guanti, Giuseppe et al., (2002) O-Protecting groups as long-range stereocontrolling elements in the addition of acetylides to 4-substituted quinolines. Tetrahedron: Asymmetry 13(24):2703-2726.

Honda, Yutaka et al., (2004) New approaches to the industrial synthesis of HIV protease inhibitors. Org. Biomol. Chem. 2(14):2061-2070.

Li, Hui-Zhang et al., (2003) A study on the sulfonation of aromatic amines with sulfuric acid under microwave irradiation. Journal of Chemical Research, Synopses 2003(8):493-494.

Miller, John F. et al., (2004) Novel arylsulfonamides possessing sub-picomolar HIV protease activities and potent anti-HIV activity against wild-type and drug-resistant viral strains. Bioorg Med Chem Lett 14(4):959-963.

Steffan, Robert J. et al., (2002) Novel substituted 4-aminomethylpiperidines as potent and selective human beta3-agonists. Part 2: arylethanolaminomethylpiperidines. Bioorg Med Chem Lett 12(20):2963-2967.

Surleraux, Dominic L. N. G. et al., (2005) Discovery and selection of TMC114, a next generation HIV-1 protease inhibitor. J Med Chem 48(6):1813-1822.

Wenger, Ronald Maurice (1985) Synthesis of Cyclosporine and Analogues: Structural Requirements for Immunosuppressive Activity. Angew. Chim. Int. Ed. Eng. 24(2):77-85.

ISR of PCT/IL2010/000533 Jun. 3, 2011.

ISR of PCT/IL2011/000079 Jun. 13, 2011.

PROCESS FOR THE PREPARATION OF DARUNAVIR AND DARUNAVIR INTERMEDIATES

CROSS REFERENCE TO RELATED APPLICATIONS

This application is a 35 U.S.C. §371 National Phase Entry Application from PCT/IL2011/000079, filed Jan. 24, 2011, and designating the United States and claims priority to U.S. Application No. 61/298,941 filed Jan. 28, 2010 and to PCT Application No. PCT/IL2010/0000533 filed Jul. 1, 2010, which are incorporated herein in their entireties.

FIELD OF THE INVENTION

The present invention relates to a process for the preparation of darunavir, a nonpeptide protease inhibitor (PI), useful for the treatment of HIV/AIDS in patients harboring multidrug-resistant HIV-1 variants that do not respond to previously existing HAART regimens. The present invention further relates to processes for the preparation of darunavir intermediates, and to certain novel intermediates obtained by such processes.

BACKGROUND OF THE INVENTION

Human immunodeficiency virus type 1 (HIV-1) infection remains a major global health problem due to the emergence of drug-resistant strains. Thus, there is an ongoing need for new therapeutics for the long-term management of HIV infection and for acute HIV-1 infection due to drug-resistant strains. HIV-1 protease inhibitors (PIs) have proven to be effective additions to existing antiretroviral regimens. However, despite the success of these agents, the emergence of mutants conferring multidrug resistance (MDR) remains a critical problem. Darunavir is a next-generation nonpeptide PI that exhibits potent antiviral activity with low toxicity in vitro and in vivo. The agent retains activity against resistant strains and has low liability for the development of resistance. Darunavir was approved by the FDA under the name PREZISTA™, and is administered in combination with a low-dose of ritonavir and other active anti-HIV agents.

The first synthesis of darunavir was described in A. K. Ghosh et al. Bioorganic & Medicinal Chemistry Letters 8 (1998) 687-690, which is herein incorporated by reference. The azido epoxide was reacted with isobutylamine in 2-propanol at 80° C. for 12 h to afford azidoalcohol. Treatment of the azidoalcohol with p-nitrobenzenesulfonyl chloride in the presence of aqueous NaHCO$_3$, provided the corresponding azide, which was hydrogenated over 10% Pd—C in ethyl acetate to afford the amine (yield of 75-78%). This amine was transformed to darunavir (I) upon reaction with hexahydrofuro[2,3-b]furan-3-yl derivative in methylene chloride in the presence of 3 equiv of triethylamine at 23° C. for 12 h with overall yield of 60-65% according to the following scheme:

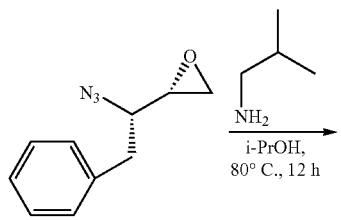

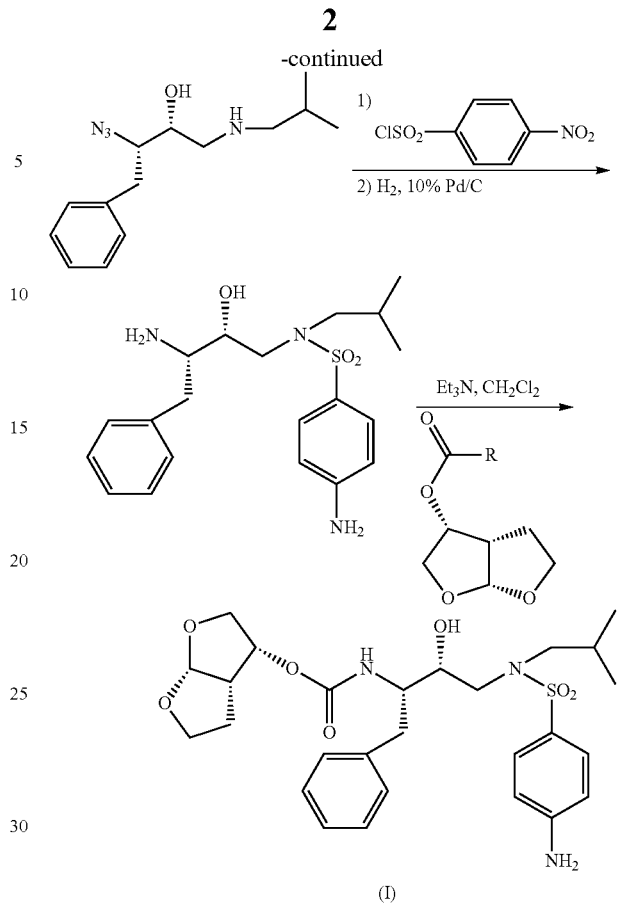

(I)

The same method is described in WO 99/067254.

Azidoepoxide is a hazard compound, which is not commercially available. Because of this, different approaches were proposed to substitute this compound with more readily available analogs. For example PCT patent applications WO 2005/063770, WO 2008/132154 disclose:

(i) amidation of (1-oxiranyl-2 phenyl-ethyl)-carbamic acid tert-butyl ester with isopropylamine according to the following scheme:

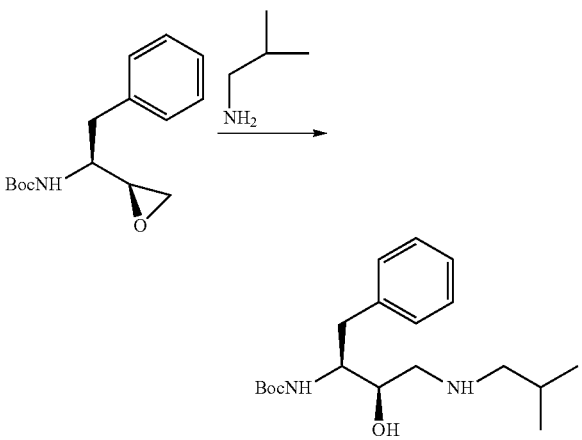

(ii) introducing a p-nitrophenylsulfonyl group in the resultant compound of step (i) according to the following scheme:

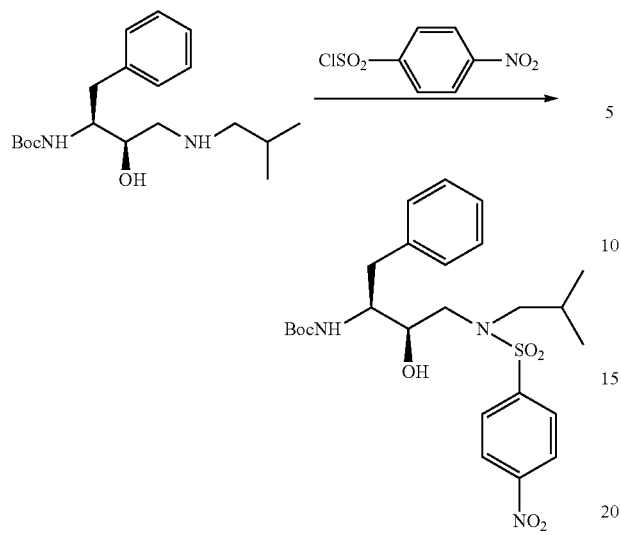

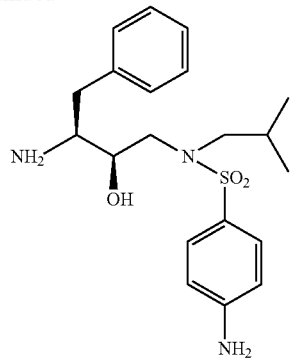

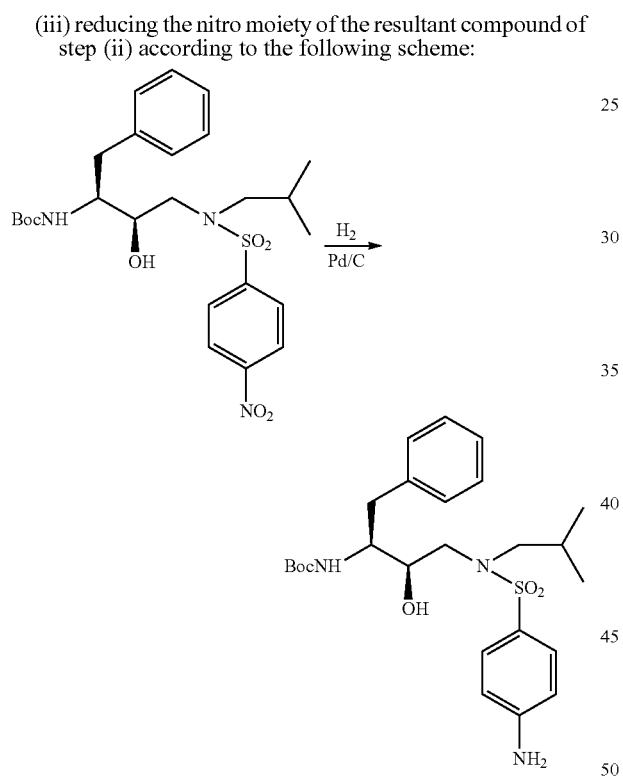

(iii) reducing the nitro moiety of the resultant compound of step (ii) according to the following scheme:

(iv) deprotecting the resultant compound of step (iii) according to the following scheme:

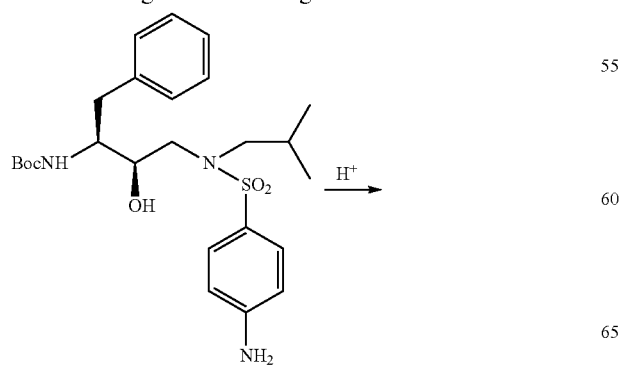

(v) Coupling the resultant compound of step (iv) with a (3R,3aS,6aR)-hexahydrofuro[2,3-b]furan-3-yl derivate, to form compound of formula (I) according to the following scheme:

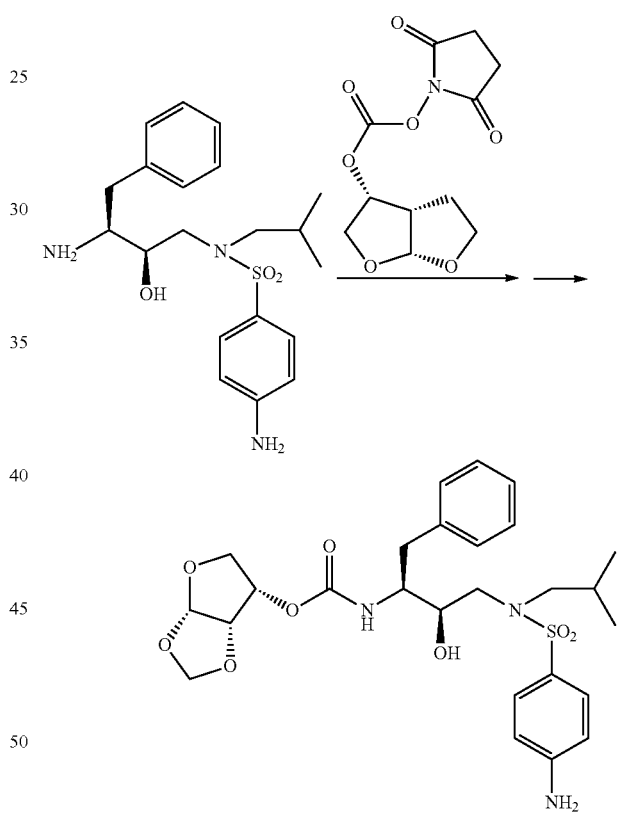

I

Although this process is more technological than the above described process [WO 99/067254], its overall yield is still moderate (50-55%). The moderate yield can be attributed to the multistage process leading to an overall unsatisfactory yield.

Consequently, there is a long-felt need for a process for the preparation of darunavir which not only overcomes the problems in the prior art processes as mentioned above, but is also safe, cost effective, and industrially feasible.

(3R,3aS,6aR)-hexahydrofuro[2,3-b]furan-3-ol is a precursor of (3R,3aS,6aR)-hexahydrofuro[2,3-b]furan-3-yl derivates and is a key intermediate for the preparation of darunavir. (3R,3aS,6aR)-hexahydrofuro[2,3-b]furan-3-ol is commercially available and may be prepared in several ways described in the literature, for example in WO 99/67254, WO 2002/060905, US 2004/127727, WO 2005/095410, WO 2003/024974, WO 2003/022853, WO 2004/033462, US 2006/148865, WO 2007/126812, US 2004/0162340 (U.S. Pat. No. 6,867,321), US 2005/256322, WO 2006/132390 (corresponding to EP 1889826), WO 2008/034598, WO 2008/055970, and Ghosh et al, J. Org. Chem. 69 (2004) 7822-7829. A common feature of some prior art processes for the preparation of (3R,3aS,6aR)-hexahydrofuro[2,3-b]furan-3-ol is the use, at different stages of the process, of protecting groups that are acid-sensitive, and therefore removed under acidic conditions. Such acidic conditions are a prerequisite of the cyclization process forming the furanol ring. Examples of protecting groups used in the synthesis of (3R,3aS,6aR)-hexahydrofuro[2,3-b]furan-3-ol include benzyl ether protecting groups, alkyl ether protective groups and silyl protecting groups.

A major disadvantage of the synthesis of (3R,3aS,6aR)-hexahydrofuro[2,3-b]furan-3-ol according to the available protocols is that the desired compound is initially obtained in the form of a diastereomer racemic mixture of hexahydrofuro[2,3-b]furan-3-ols. Optical resolution methods are generally inefficient and expensive. Examples include (i) optical resolution carried out by enzymes, this reaction is inefficient since only one of the resulting enantiomers is used for the production of an intended substance, while the other enantiomer is discarded; (ii) using an optically active form as a raw material, this option is non-economical as optically active compounds are expensive; (iii) conversion of the racemic mixture into the corresponding acetate followed by enzymatic hydrolysis; and (iv) oxidizing the racemic mixture followed by a reducing step. Another clear disadvantage of the available procedures is the simultaneous deprotection (intermolecular reaction) and ring closure processes (intramolecular reaction) which take place under acidic conditions and result in reduced product yields.

Thus, there is an unmet need for a process for the synthesis of an optically active (3R,3aS,6aR)-hexahydrofuro[2,3-b]furan-3-ol, which is efficient and inexpensive.

SUMMARY OF THE INVENTION

According to a first aspect, the present invention provides a process for the preparation of darunavir, a compound of formula (I) (chemically designated [(1S,2R)-3-[[(4-aminophenyl)sulfonyl](2-methylpropyl)amino]-2-hydroxy-1-(phenylmethyl) propyl]-carbamic acid (3R,3aS,6aR)hexahydrofuro[2,3-b]furan-3-yl ester). As contemplated herein, the applicants of the present invention have discovered a process by which the compound of formula (I) may be prepared on a manufacturing scale from the compound

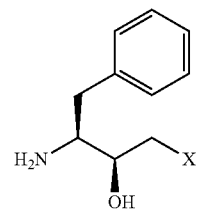

II wherein X is a leaving group. Non-limiting examples of leaving groups include a halogen (e.g., Cl, Br, I) or a sulfonate leaving group (e.g., MsO and TsO). According to some embodiments, X is Cl.

By using the process according to embodiments of the present invention, the compound of formula (I) can be synthesized in only three distinct stages instead of five as previously described. According to some embodiments, the first and the second stages are performed together in a single step. According to other embodiments, the entire process can be performed as "one-pot" synthesis. Each possibility represents a separate embodiment of the present invention.

In addition to the associated benefits of fewer stages, such as time and cost savings, the improved process reduces the amount of waste products formed. Furthermore, product may be obtained in a higher yield, e.g., approximately 80-90%.

The process of the present invention involves the synthesis of compound of formula (I) starting from the compound of formula (II) comprising the following steps:

(i) reacting a 3-amino-2-hydroxy-4-phenylbutane derivative of formula (II), wherein X is a leaving group, with (3R,3aS,6aR)-hexahydrofuro[2,3-b]furan-3-yloxy carbonyl derivative of formula (III), wherein R is selected from the group consisting of halogen, imidazolyl, benzotriazolyl, oxysuccinimidyl, oxybenzotriazolyl, 4-nitrophenoxy, 4-methoxyphenoxy, 2-nitrophenoxy and pentafluorophenoxy to obtain a compound of formula (IV):

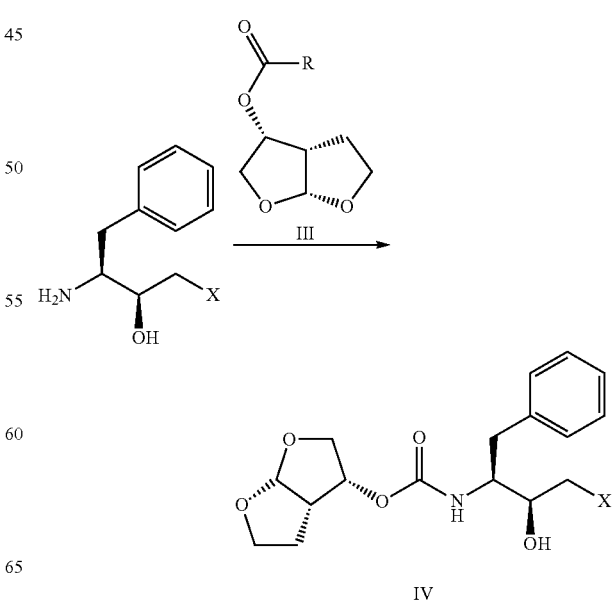

(ii) reacting the resultant compound (IV) with isobutylamine, to obtain a compound of formula (V);

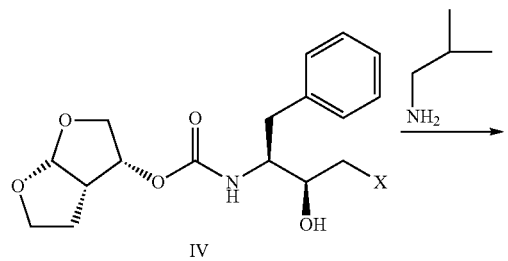

and (iii)—reacting the resultant compound of formula (V) with a substituted phenylsulfonyl derivative (e.g., phenylsulfonyl chloride) to form a compound of formula (I) (Darunavir, chemically designated [(1S,2R)-3-[[(4-aminophenyl)sulfonyl](2-methylpropyl)amino]-2-hydroxy-1-(phenylmethyl) propyl]-carbamic acid (3R,3aS,6aR)hexahydrofuro[2,3-b] furan-3-yl ester).

subsequently prepared from compounds which are prepared in accordance with certain embodiments of the present invention.

The compound of formula (II) can be used as a free base or, according to some embodiments, in the form of salt. According to certain embodiments the salt is a hydrochloride salt. The compound of formula (II) may be prepared by several ways available in the literature.

In one embodiment, the compound of formula (II) is coupled with a hexahydrofuro[2,3-b]furan-3-yl derivative (III) to obtain compound of formula (IV).

wherein R is halogen (e.g., Cl, Br, I), imidazolyl, benzotriazolyl, oxysuccinimidyl, oxybenzotriazolyl, 4-nitrophenoxy, 4-methoxyphenoxy, 2-nitrophenoxy, pentafluorophenoxy or other analogous groups typically used for formation of active esters.

The compound of formula (III) can be prepared from (3R, 3aS,6aR)-hexahydrofuro[2,3-b]furan-3-ol in a conventional manner, for example as described in WO 2005/000249. The (3R,3aS,6aR)-hexahydrofuro[2,3-b]furan-3-ol is suitably

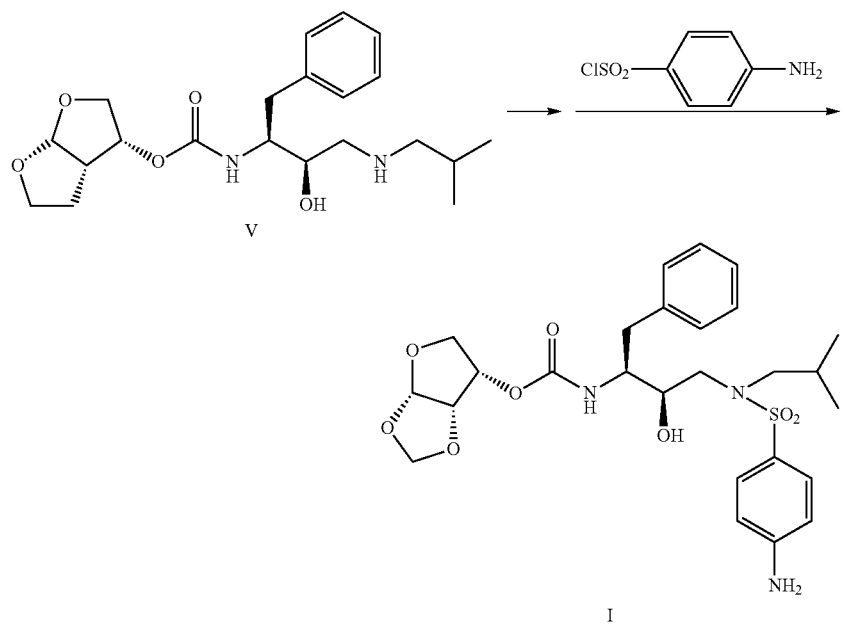

The above schemes are provided for illustration only and are not intended to limit the scope of the present invention.

According to one embodiment, the tetrahydrofuranol derivative (III) is prepared and coupled with the compound (II) in a single step.

The present invention also relates to the stereoisomeric forms of the compounds employed in the process according to the invention including starting materials and compounds activated with a coupling agent to generate a hexahydrofuro [2,3-b]furan-3-yl derivative (III) which is then coupled with the compound of formula (II) to obtain the compound (IV).

Non-limiting examples of coupling agents that may be used in the preparation of compound (III) are carbonates such as bis-(4-nitrophenyl)carbonate, and disuccinimidyl carbonate (DSC), carbonyl diimidazole (CDI), chloroformates, such as p-nitrophenylchloroformate, phosgene or triphosgene.

According to some embodiments, step (ii) is carried out by reacting the compound of formula (IV) with isobutylamine to form compound (V), with isobutylamine as solvent or in a suitable solvent including, but not limited to an alcohol (e.g., ethanol), an ester (e.g., ethyl acetate), an ether (e.g., THF), a chlorinated solvent (e.g., dichloromethane) and other solvents such as acetonitrile or toluene or mixtures of these solvents with each other or with water. According to some currently preferred embodiments, the reaction is carried out by mixing a THF solution of compound (IV) with isobutylamine in the presence of a base, such as inorganic base including, but not limited to sodium hydroxide, sodium hydrogen carbonate, soda ash and, potassium or sodium carbonate or an organic base such as a tertiary amine, selected from the group consisting of acyclic amines (e.g., trimethylamine, triethylamine, dimethylphenylamine diisopropylethylamine and tributylamine), cyclic amines (e.g., N-methylmorpholine) and aromatic amines (dimethylaniline, dimethylaminopyridine and pyridine). According to one embodiment, an excess of isobutylamine can be used as a base. According to some embodiments, the reaction is carried out at a temperature in the range of about 50° C. to reflux temperature, wherein the reflux temperature depends on the boiling point of the solvent used.

According to some embodiments, reaction steps (i) and (ii) can be carried out in a single step without the separation of compound (IV).

According to some embodiments, step (iii) is carried out by reacting the compound of formula (V) with a substituted phenylsulfonyl derivative such as a substituted phenylsulfonyl halide, for example, p-aminobenzenesulfonyl chloride, in a suitable solvent selected from a ketone (e.g., acetone), an ester (e.g., ethyl acetate), an ether (e.g., THF), an amide (e.g., dimethylformamide or dimethylacetamide), a chlorinated solvent (e.g., dichloromethane) and other solvents such as acetonitrile or toluene or mixtures thereof or mixtures of any of these solvents with water. According to some embodiments, the reaction is carried out at a temperature in the range of about 20° C. to reflux temperature, wherein the reflux temperature depends on the boiling point of the solvent used. According to some currently preferred embodiments, the reaction is carried out at a temperature in the range of about 20-35° C. and in the presence of a base selected from inorganic base (e.g., sodium hydroxide, sodium hydrogen carbonate, soda ash, and potassium carbonate), organic base (e.g. tertiary amine, including acyclic amines (e.g., trimethylamine, triethylamine, diisopropylamine, tributylamine), cyclic amines (e.g., N-methylmorpholine) and aromatic amines (e.g., dimethylaniline, dimethylaminopyridine and pyridine).

According to some embodiments, the steps (i), (ii) and (iii) can be combined and carried out in a single step without the need to separate intermediate compounds.

The applicants further disclose herein a novel and effective process for the stereoselective synthesis of (3R,3aS,6aR)-hexahydrofuro[2,3-b]furan-3-ol, which is a precursor for the preparation of compound of formula (III) which in turn is a precursor for the preparation of darunavir of formula (I). Thus, according to a further aspect, the present invention provides a process for the stereo-directed synthesis of (3R,3aS,6aR)-hexahydrofuro[2,3-b]furan-3-ol comprising the steps of:

(a) reacting an ethanol derivative of the general formula HO—CH$_2$—CH$_2$—X$^1$, with a reagent comprising a stereo-controlling (stereo-directing) moiety (Y$^1$) to obtain a compound having the formula (VI):

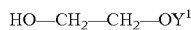    VI wherein X$^1$ is OH or a leaving group and the stereodirecting moiety Y$^1$ is removable under neutral or basic conditions;

(b) oxidizing compound (VI) to obtain an aldehyde having the formula (VII);

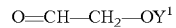    VII (c) reacting a butanol derivative of the general formula HO—(CH$_2$)$_4$—X$^2$, with a reagent comprising a stereo-directing moiety (Y$^2$) to obtain a compound having the formula (VIII);

    VIII wherein X$^2$ is OH or a leaving group and the stereodirecting moiety Y$^2$ is removable under neutral or basic conditions;

(d) oxidizing compound (VIII) to obtain an aldehyde having the formula (IX);

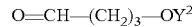    IX (e) stereoselectively coupling compounds (VII) and (IX) in the presence of a chiral catalyst to form a compound of formula (X);

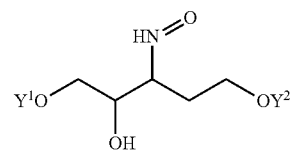    X wherein the coupling step is preferably by aldol condensation; and (f) removing the stereodirecting moieties (Y$^1$ and Y$^2$) from the product of step (e) followed by cyclization in the presence of a catalyst (preferably an acid catalyst) to form (3R,3aS,6aR)-hexahydrofuro[2,3-b]furan-3-ol.

According to some embodiments, X$^1$ and X$^2$ are each independently OH or a leaving group. Non-limiting examples of suitable leaving groups include halogens (e.g., Cl, Br, I), or sulfonate leaving groups (e.g., MsO and TsO). According to an exemplary embodiment, X$^1$ and X$^2$ are each OH.

According to some embodiments, Y$^1$ and Y$^2$ are each independently a stereo-directing moiety that can be removed under basic or neutral conditions. In currently preferred embodiments, Y$^1$ and Y$^2$ are bulky groups. Non-limiting examples of stereo-directing moieties that can be removed under basic or neutral conditions include fluorenylmethyloxycarbonyl (Fmoc), p-nitrobenzenesulfoethoxycarbonyl, propargyloxycarbonyl, picolinyl, prenyl, o-nitrobenzyloxy methyl, 4-methyoxyphenoxymethyl, guaiacolmethyl, siloxymethyl, such as triisopropylsiloxymethyl, 2-cyanoethyoxymethyl, 2-quinolinylmethyl, dichloroacetyl, trichloroacetyl, and 2-[4-nitrophenyl]ethylsulfonate. Each possibility represents a separate embodiment of the present invention. According to some currently preferred embodiments, the stereodirecting moiety is Fmoc. According to other embodiments, the stereodirecting moiety is not a benzyl ether protecting group, an alkyl ether protective group or a silyl protecting group.

X$^1$ and X$^2$ may be the same or different from each other. Y$^1$ and Y$^2$ may be the same or different from each other.

Without wishing to be bound by theory or mechanism of action, it is contemplated that the bulkiness of the stereodirecting groups influences the stereochemistry of aldol condensation towards the desired isomer, i.e., the (3R,3aS,6aR)-hexahydrofuro[2,3-b]furan-3-ol stereoisomer. It is contemplated that replacing the acid-labile protecting groups known in the art with a bulky stereodirecting group such as Fmoc or similar groups (e.g. p-nitrobenzenesulfoethoxycarbonyl) has the following advantages: (a) Fmoc derivatives have in general the tendency to form crystals in contrast to the acid-labile protecting groups mentioned in the art; (b) because of strong UV absorption of the Fmoc group, the control of the reaction by TLC and HPLC is easier; (c) removal of Fmoc group is simple and quantitative at neutral conditions (for example, by using of catalytic amount of DBU or fluoride anions as tetrabutylammonium fluoride and pyridine hydrogen fluoride); and above all (d) the presence of bulky Fmoc group will help to perform reaction in the right stereoselective direction.

According to some currently preferred embodiments, the oxidation of compounds VI and VIII is performed by $SO_3$-pyridine complex in the presence of triethylamine.

The solvent in which the process for the preparation of (3R,3aS,6aR)-hexahydrofuro[2,3-b]furan-3-ol takes place is not particularly restricted provided it does not interfere with the reaction. Non-limiting examples of suitable solvents include aliphatic hydrocarbon solvents, aromatic solvents, ether solvents, alcohol solvents, ester solvents, water, chlorinated hydrocarbons, protic polar solvents, aprotic polar solvents, mixed solvents, ionic liquids thereof and the like, and any mixtures thereof. Each possibility represents a separate embodiment of the present invention.

The compounds represented by the structures VI, VII and IX wherein $Y^1$ and $Y^2$ are both Fmoc are novel compounds and are claimed as such.

According to another aspect, the present invention provides the use of compounds having the structures VI, VII, VIII and IX for the preparation of (3R,3aS,6aR)-hexahydrofuro[2, 3-b]furan-3-ol. According to some embodiments, the process further comprises the step of converting (3R,3aS,6aR)-hexahydrofuro[2,3-b]furan-3-ol to darunavir of formula (I). According to some currently preferred embodiments, the present invention provides the use of compounds having the structures VI, VII, and IX wherein $Y^1$ and $Y^2$ are both Fmoc for the preparation of (3R,3aS,6aR)-hexahydrofuro[2,3-b]furan-3-ol. According to other currently preferred embodiments, the present invention provides the use of compounds having the structures VI, VII, VIII and IX wherein $Y^1$ and $Y^2$ are both Fmoc for the preparation of (3R,3aS,6aR)-hexahydrofuro[2,3-b]furan-3-ol.

According to some embodiments, the stereoselective aldol condensation is performed in the presence of a chiral catalyst. According to some embodiments, the chiral catalyst is selected, yet not limited to chiral amino acids and their derivatives, for example, organic and inorganic salts, complexes with metals or peptides. According to one embodiment, the chiral catalyst is a valine. According to another embodiment, the chiral catalyst is a dipeptide. According to yet another embodiment, the chiral catalyst is other than proline. According to yet another embodiment, the chiral catalyst is chiral cyclic secondary amine, preferably, proline or 5,5-dimethyl thiazolidinium-4-carboxylic acid. Each possibility represents a separate embodiment of the present invention.

According to some embodiments, the removal of the stereodirecting moieties ($Y^1$ and $Y^2$) from the product of the stereoselective aldol condensation is performed under basic conditions; alternatively under mild basic conditions; alternatively under neutral conditions, each possibility representing a separate embodiment of the present invention. According to currently preferred embodiments, the stereodirecting moieties may be removed under neutral conditions by 1,8-Diazabicycloundec-7-ene (DBU) or by a fluoride anion such as tetrabutylammonium fluoride or pyridine hydrogen fluoride. According to another embodiment, the removal of the stereodirecting moieties may be performed under conditions well known in the art.

The cyclization of the $Y^1$ and $Y^2$ eliminated product to obtain (3R,3aS,6aR)-hexahydrofuro[2,3-b]furan-3-ol is preferably carried out in the presence of an acid catalyst. Non-limiting examples of acid catalysts include Lewis acids such as zinc chloride, aluminium chloride, titanium tetrachloride and the like, inorganic acids, such as hydrochloric acid, hydrofluoric acid, sulfuric acid, tungstic acid, organic acids, such as methanesulfonic acid, p-toluenesulfonic acid, and solid acids, such as acidic ion exchange resins or zeolites.

According to some embodiments, the process for the preparation of (3R,3aS,6aR)-hexahydrofuro[2,3-b]furan-3-ol further comprises the conversion of (3R,3aS,6aR)-hexahydrofuro[2,3-b]furan-3-ol to darunavir of formula (I).

The following examples further describe and demonstrate particular embodiments within the scope of the present invention. The examples are given solely for illustration and are not to be construed limitations as many variations are possible without departing from the spirit and scope of the invention.

It will be appreciated that desirably reactions described herein are carried out for a time and under conditions sufficient to produce the desired product, preferably in an optimum yield.

It is intended that each of the patents, applications, and printed publications, including books, mentioned in this patent document be hereby incorporated by reference in their entirety.

DETAILED DESCRIPTION OF THE INVENTION

According to a first aspect, the present invention provides a process for the preparation of darunavir, a compound of formula (I). The process involves the synthesis of compound of formula (I) starting from the 3-amino-2-hydroxy-4-phenylbutane derivative of formula (II), comprising the following steps: (i) coupling (II) with a (3R, 3aS,6aR)-hexahydrofuro[2,3-b]furan-3-yl derivate (III), (ii)—reacting the resultant compound (IV) with isobutylamine, and (iii)—coupling the resultant compound (V) with a phenylsulfonyl derivative to form a compound of formula (I). Compound (III) may be prepared by reacting (3R,3aS,6aR)-hexahydrofuro[2, 3-b]furan-3-ol with a suitable coupling reagent. The present invention further provides a process for preparing (3R,3aS, 6aR)-hexahydrofuro[2,3-b]furan-3-ol.

Step (i)

Step (i) involves the coupling of 3-amino-2-hydroxy-4-phenylbutane derivative (compound of formula (II)) with a (3R,3aS,6aR)-hexahydrofuro[2,3-b]furan-3-yl derivate (III) to obtain compound of formula (IV).

According to some embodiments, the X moiety in the compound of formula (II) is a labile leaving group. Labile leaving groups suitable for use in the present invention include a sulfonate leaving group such as mesylate ($-OSO_2CH_3$); $-OSO_2(C_nH_{2n+1})$, wherein n=0-4; $-OSO_2-R^P$, where $R^P$ is an optionally substituted phenyl group (e.g. 4-Me-Ph, tosylate); lower alkanoate such as acetate, a halogen (e.g., I, Br, Cl), or $-N^+Me_3X^-$, wherein X may be —OTf, —OTs, —I, —Br, —Cl or —OH. Each possibility represents a separate embodiment of the present invention. According to some currently preferred embodiments, X is Cl.

According to some embodiments of the present invention step (i) is carried out by reacting the compound of formula (II) with a (3R,3aS,6aR)-hexahydrofuro[2,3-b]furan-3-yl derivate, for example in an organic solvent selected from a ketone (e.g., acetone), an ester (e.g., ethyl acetate), an ether (e.g., THF), an amide (e.g., dimethylformamide or dimethylacetamide), a chlorinated solvent (e.g., dichloromethane) and other solvents such as acetonitrile or toluene or mixtures thereof. According to some currently preferred embodiments, the organic solvent is dichloromethane or THF. According to some embodiments, the (3R,3aS,6aR)-hexahydrofuro[2,3-b]furan-3-yl derivate is (3R,3aS,6aR) hexahydrofuro[2,3-b]furan-3-yl imidazolyl carbonate. According to other embodiments, the (3R,3aS,6aR)-hexahydrofuro[2,3-b]furan-3-yl derivate is (3R,3aS,6aR) hexahydrofuro[2,3-b]furan-3-yl oxysuccinimide carbonate. According to some embodiments, the reaction is carried out at a temperature in the range of about 20° C. to reflux temperature, wherein the reflux temperature depends on the boiling temperature of the solvent used. According to a currently preferred embodiment, the reaction is carried out at a temperature in the range of about 20-60° C., with dichloromethane or THF as the preferred solvent.

According to one preferred embodiment, X in the compound of formula (II) is Cl. In accordance with this embodiment, the compound of formula (II) is designated (2S,3S)-3-amino-1-chloro-2-hydroxy-4-phenylbutane.

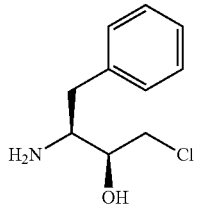 [SMILES: N[C@@H](Cc1ccccc1)[C@H](O)CCl]

The compound of formula (II) can be used as a free base or, according to some embodiments, in the form of salt. According to certain embodiments, the salt is a hydrochloride salt. Some of the compounds of formula (II) are commercially available (e.g., (2S,3S)-3-amino-1-chloro-2-hydroxy-4-phenylbutane hydrochloride).

Alternatively, compounds of formula (II) may be prepared by several ways available in the literature (for example see a) Tetrahedron Letters, 1995, 36(19); 3317-20 and b) Org. Biomol. Chem., 2004, 2:2061-70).

According to some embodiments, the R moiety in the compound of formula (III) is halogen (e.g., —F, —Cl, —Br, —I), imidazolyl, benzotriazolyl, oxysuccinimidyl, oxybenzotriazolyl, 4-nitrophenoxy, 4-methoxyphenoxy, 2-nitrophenoxy, pentafluorophenoxy or other analogous groups, usually used for formation of active esters.

The compound of formula (III) above can be prepared from (3R,3aS,6aR)-hexahydrofuro[2,3-b]furan-3-ol in a conventional manner, for example as described in WO 2005/000249. The (3R,3aS,6aR)-hexahydrofuro[2,3-b]furan-3-ol is suitably activated with a coupling agent RCO—Y wherein Y is a leaving group such as described above for the substituents X, to generate a hexahydrofuro[2,3-b]furan-3-yl derivative (III) which is then coupled with the compound of formula (II) to obtain the compound (IV).

Non-limiting examples of coupling agents that may be used in the preparation of compound (III) are carbonates such as bis-(4-nitrophenyl)carbonate, disuccinimidyl carbonate (DSC), vinylene carbonate, ethylene carbonate, $C_1$-$C_4$ dialkyl carbonate and 2-(S),3-pyridinediyl carbonate; chloroformates such as phenyl chloroformate, trichloromethyl chloroformate, phenyl tetrazoylformate and p-nitrophenylchloroformate; carbonyl diimidazole (CDI); oxalyl chloride (ethanedioyl dichloride); phosgene; diphosgene or triphosgene.

For example, (3R,3aS,6aR)-hexahydrofuro[2,3-b]furan-3-yl-imidazolylcarbonate (compound of formula IIIA) is obtained upon reaction of (3R,3aS,6aR)-hexahydrofuro[2,3-b]furan-3-ol with carbonyl diimidazole,

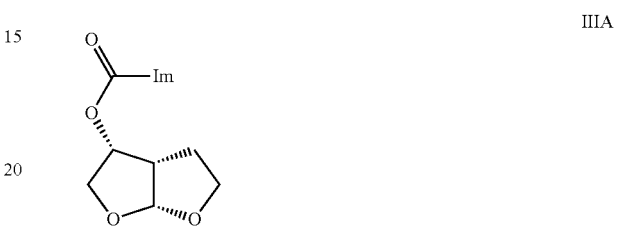

Alternatively, (3R,3aS,6aR)-hexahydrofuro[2,3-b]furan-3-yl-oxysuccinimide carbonate (compound of formula IIIB) is obtained upon reaction of (3R,3aS,6aR)-hexahydrofuro[2, 3-b]furan-3-ol with disuccinimidyl carbonate (DSC):

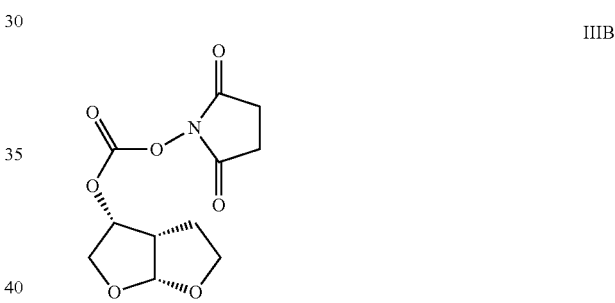

Step (ii)

According to some embodiments, step (ii) is carried out by reacting the compound of formula (IV) with isobutylamine to form compound (V), with isobutylamine as a solvent or in a suitable solvent including, but not limited to an alcohol (e.g., ethanol), an ester (e.g., ethyl acetate), an ether (e.g., THF), a chlorinated solvent (e.g., dichloromethane) and other solvents such as acetonitrile or toluene or mixtures of these solvents with each other or with water. According to some currently preferred embodiments, the reaction is carried out by mixing a THF solution of compound (IV) with isobutylamine in the presence of a base, such as inorganic base including, but not limited to sodium hydroxide, sodium hydrogen carbonate, soda ash and, potassium or sodium carbonate or an organic base such as a tertiary amine, selected from the group consisting of acyclic amines (e.g., trimethylamine, triethylamine, dimethylphenylamine, diisopropylethylamine and tributylamine), cyclic amines (e.g., N-methylmorpholine) and aromatic amines (dimethylaniline, dimethylaminopyridine and pyridine). According to one embodiment, an excess of isobutylamine can be used as a base. According to some embodiments, the reaction is carried out at a temperature in the range of about 50° C. to reflux, wherein the reflux temperature depends on the boiling point of the solvent used.

According to some embodiments, reaction steps (i) and (ii) can be carried out in a single step without the separation of compound (IV). According to other embodiments, the synthesis of compound of formula (III), step (i) and step (ii) can be carried out in a single step without the separation of compound (III) or compound (IV).

Step (iii)

According to some embodiments step (iii) is carried out by reacting the compound of formula (V) with a substituted phenylsulfonyl halide, for example, p-aminobenzenesulfonyl chloride, in a suitable solvent selected from a ketone (e.g., acetone), an ester (e.g., ethyl acetate), an ether (e.g., THF), an amide (e.g., dimethylformamide or dimethylacetamide), a chlorinated solvent (e.g., dichloromethane) and other solvents such as acetonitrile or toluene or mixtures thereof or mixtures of any of these solvents with water. According to some embodiments, the reaction is carried out at a temperature in the range of about 30° C. to reflux temperature, wherein the reflux temperature depends on the boiling point of the solvent used. According to some currently preferred embodiments, the reaction is carried out at a temperature in the range of about 20-35° C. and in the presence of a base selected from inorganic base (e.g., sodium hydroxide, sodium hydrogen carbonate, soda ash, and potassium carbonate), organic base (e.g., tertiary amine, including acyclic amines (e.g., trimethylamine, triethylamine, diisopropylamine, tributylamine), cyclic amines (e.g., N-methylmorpholine) and aromatic amines (e.g., dimethylaniline, dimethylaminopyridine and pyridine).

Benzenesulfonyl derivatives such as, p-aminobenzenesulfonyl chloride, are known in the art, for example, for the preparation of $b_3$ adrenoreceptor agonists (R. J. Steffan e.a. Bioorganic & Medicinal Chemistry Letters, 12 (2002) 2963-2967). Benzenesulfonyl derivatives may be produced by the methods described in British Polymer Journal (1980), 12(4), 192-8, JP09124629, Journal of Chemical Research, Synopses, (8), 493-494; 2003.

According to some embodiments, steps (i), (ii) and (iii) can be combined and carried out in a one-pot reaction without the need to separate intermediate compounds. According to other embodiments, the synthesis of compound of formula (III), steps (i), (ii) and (iii) can be combined and carried out in a one-pot reaction without the need to separate intermediate compounds.

According to some further embodiments, the reaction of step (iii) may be used for the preparation of analogs and derivatives of compound (I) examples of which were found to be potent biological active compounds, especially as HIV protease inhibitors, for example, J. F. Miller et al. Bioorganic & Medicinal Chemistry Letters 14 (2004) 959-963; WO 2005/110428, WO 2007/060253; WO 2005/087728 and WO 2004/016619.

Process for the Synthesis of (3R,3aS,6aR)-hexahydrofuro[2,3-b]furan-3-ol

The applicants of the present invention further disclose herein a novel and an effective process for the stereoselective synthesis of (3R,3aS,6aR)-hexahydrofuro[2,3-b]furan-3-ol, which is a precursor for the preparation of compound of formula (III).

WO 2006/132390 discloses the synthesis of (3R,3aS,6aR)-hexahydrofuro[2,3-b]furan-3-ol, via a reaction of protected 2-oxyacetaldehyde with protected 4-oxybutylaldehyde in the presence of cyclic secondary amine, namely, L-proline, followed by a simultaneous removal of the protecting groups by acid and cyclization of formed hydroxyaldehyde derivative to hexahydrofuro[2,3-b]furan-3-ol. To obtain a pure stereoisomer as (3R,3aS,6aR)-hexahydrofuro[2,3-b]furan-3-ol, the furan-3-ol prepared as described above was subsequently converted to hexahydrofuro[2,3-b]furan-3-one, purified by crystallization and reduced to the desired compound with sodium borohydride.

In order to obtain the isomer (3R,3aS,6aR)-hexahydrofuro[2,3-b]furan-3-ol with high stereopurity and to eliminate additional steps of purification, the applicants hereby have invented a process for the synthesis of (3R,3aS,6aR)-hexahydrofuro[2,3-b]furan-3-ol, using aldehydes containing stereocontrolling functional groups.

General principles of chiral auxiliary design using stereocontrolling groups is described in Pure & App. Chem., Vol. 70, No. 8, pp. 1501-1506, 1998. According to these principles, the process of using stereocontrolling groups differs significantly from a process which involves the use of protecting groups. Unlike common protecting groups, stereocontrolling groups do not act simply as passive spectators; stereocontrolling groups are chiral and conformationally flexible, attributes which enable them to be inserted between the stereogenic centre (also known as the 'chiral center') and the prochiral reactive center. Steric interactions between the functional group of the stereogenic centre and the stereocontrolling group serve to fixate the relative 1,2-stereochemistry antiperiplanar of the intermediate, thus directing any incoming reactant at the prochiral center located anti to the conformationally mobile group.

The terms "isomer", "isomeric form", "stereochemically isomeric forms" or "stereoisomeric forms", as used herein, define all possible isomeric as well as conformational forms, made up of the same atoms bonded by the same sequence of bonds but having different three-dimensional structures which are not interchangeable, which compounds or intermediates obtained during said process may possess. Isomers include diastereoisomers, epimers, enantiomers and/or conformers of the basic molecular structure of said compound. More in particular, stereogenic centers (also referred to as chiral centers) may have the R- or S-configuration, diastereoisomers may have a syn- or anti-configuration, substituents on bivalent cyclic saturated radicals may have either the cis- or trans-configuration and alkenyl radicals may have the E or Z-configuration.

The term "diastereomer" or "diastereomeric form" applies to molecules with identical chemical constitution and containing more than one stereocenter, which differ in configuration at one or more of these stereocenters.

The term "epimer" in the present invention refers to molecules with identical chemical constitution and containing more than one stereocenter, but which differ in configuration at only one of these stereocenters.

Pure stereoisomeric forms refer to isomers substantially free of other enantiomeric or diastereomeric forms of the same basic molecular structure of said compounds or starting material. Suitably, the terms "stereoisomerically pure" compounds or "stereopure compound" relate to compounds having a stereoisomeric excess of at least about 50% (i.e. minimum of about 75% of one isomer and maximum of about 25% of the other possible isomers) up to a stereoisomeric excess of about 100% (i.e. about 100% of one isomer and none of the other), preferably, compounds having a stereoisomeric excess of about 75% up to about 100%, more preferably, compounds having a stereoisomeric excess of about 90% up to about 100%, even more preferred compounds having a stereoisomeric excess of about 94% up to about 100% and most preferred, having a stereoisomeric excess of about 97% up to about 100%. The terms "enantiomerically pure" and "diastereomerically pure" are similarly defined, but refer to the enantiomeric or diastereomeric excess, respectively of the mixture in question.

The terms "stereocontrolling group" or "stereodirecting group" may be used interchangeably and refer to chemical groups, which when present during a chemical reaction control or direct the chemical process in such a way as to obtain a reaction product which is highly stereo-pure. Non-limiting examples of stereo-controlling or stereo-directing groups include: fluorenylmethyloxycarbonyl (Fmoc), p-nitrobenzenesulfoethoxycarbonyl, propargyloxycarbonyl, picolinyl, prenyl, o-nitrobenzyloxy methyl, 4-methyoxyphenoxymethyl, guaiacolmethyl, siloxymethyl, such as triisopropylsiloxymethyl, 2-cyanoethyoxymethyl, 2-quinolinylmethyl, dichloroacetyl, trichloroacetyl and 2-[4-nitrophenyl]ethylsulfonate (See for example, Tetrahedron: Asymmetry, 2002, 13(24) 2703-26; Pure & App. Chem., 1998, 70 (8), pp. 1501-1506).

The process for the stereo-directed synthesis of (3R,3aS, 6aR)-hexahydrofuro[2,3-b]furan-3-ol according to some embodiments of the present invention comprises the following steps:

(a) reacting an ethanol derivative of the general formula HO—$CH_2$—$CH_2$—$X^1$, with a reagent comprising a stereocontrolling (stereodirecting) moiety ($Y^1$) to obtain a compound having the formula (VI):

HO—$CH_2$—$CH_2$—$OY^1$      VI wherein $X^1$ is OH or a leaving group and the stereodirecting moiety $Y^1$ is preferably removable under neutral or basic conditions;

(b) oxidizing compound (VI) to obtain an aldehyde having the formula (VII);

O=CH—$CH_2$—$OY^1$      VII (c) reacting butanol derivative of the general formula HO—$(CH_2)_4$—$X^2$ with a reagent comprising a stereodirecting moiety ($Y^2$) to obtain a compound having the formula (VIII)

HO—$(CH_2)_4$—$OY^2$      VIII;

wherein $X^2$ is OH or a leaving group and the stereodirecting moiety $Y^2$ is preferably removable under neutral or basic conditions;

(d) oxidizing compound (VIII) to obtain an aldehyde having the formula (IX);

O=CH—$(CH_2)_3$—$OY^2$      IX (e) stereoselectively coupling compounds (VII) and (IX), preferably by aldol condensation in the presence of a chiral catalyst to form a compound of formula (X);

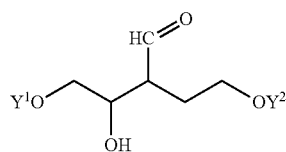

X and (f) removing the stereodirecting moieties ($Y^1$ and $Y^2$) from the product of step (e) followed by cyclization in the presence of a catalyst (preferably an acid catalyst) to form (3R,3aS,6aR)-hexahydrofuro[2,3-b]furan-3-ol.

Step (a) and Step (c)

According to some embodiments, $X^1$ and $X^2$ are each independently OH or a labile leaving group. Non-limiting examples of suitable labile leaving groups include halogens (e.g., Cl, Br, I) or sulfonate leaving groups such as mesylate (—$OSO_2CH_3$); —$OSO_2(C_nH_{2n+1})$, wherein n=0-4; —$OSO_2$—$R^P$, where $R^P$ is an optionally substituted phenyl group (e.g. 4-Me-Ph, tosylate); lower alkanoate such as acetate, or —$N^+Me_3X^-$, wherein X may be —OTf, —OTs, —I, —Br, —Cl or —OH. Each possibility represents a separate embodiment of the present invention. According to an exemplary embodiment, both $X^1$ and $X^2$ are OH.

According to some embodiments, $Y^1$ and $Y^2$ are each independently a stereodirecting moiety that can be removed under basic or neutral conditions. According to some other embodiments, $Y^1$ and $Y^2$ may also be removed under acidic conditions.

In currently preferred embodiments, $Y^1$ and $Y^2$ are bulky groups. Non-limiting examples of a stereodirecting moiety that can be removed under basic or neutral conditions include fluorenylmethyloxycarbonyl (Fmoc), p-nitrobenzenesulfoethoxycarbonyl, propargyloxycarbonyl, picolinyl, prenyl, o-nitrobenzyloxy methyl, 4-methyoxyphenoxymethyl, guaiacolmethyl, siloxymethyl, such as triisopropylsiloxymethyl, 2-cyanoethyoxymethyl, 2-quinolinylmethyl, dichloroacetyl, trichloroacetyl and 2-[4-nitrophenyl]ethylsulfonate. Each possibility represents a separate embodiment of the present invention. According to some currently preferred embodiments, the stereodirecting moiety is Fmoc. According to some other embodiments, the stereodirecting moiety is not a benzyl ether protecting group, an alkyl ether protective group or a silyl protecting group.

To introduce the stereodirecting groups $Y^1$ and $Y^2$, the precursors of formula HO—$CH_2$—$CH_2$—$X^1$ or HO—$(CH2)_4$—$X^2$ are reacted with a reagent containing the groups $Y^1$ or $Y^2$. For example, when a fluorenylmethyloxycarbonyl (Fmoc) group is used, the reagent can be fluorenylmethyloxycarbonyl chloride or anhydride. Other reagents that can be used to introduce the bulky stereodirecting groups include, but are not limited to p-nitrobenzenesulfoethoxycarbonyl chloride, propargyloxycarbonyl chloride, picolinoyl chloride, prenyl chloride, (2-nitrophenyl)methoxymethyl, 4-(methyoxyphenoxy)-methyl chloride, guaiacolmethyl chloride, siloxymethyl chloride, triisopropylsiloxymethyl chloride, 2-cyanoethyoxymethyl chloride, 2-quinolinylmethyl chloride, dichloroacetyl chloride, trichloroacetyl chloride and 2-[4-nitrophenyl]ethylsulfonyl chloride.

According to some embodiments, the reaction of steps (a) and (c) is preferably carried out at ambient temperature (i.e., about 20-25° C.) and in the presence of a base selected from organic base (e.g., tertiary amine, including acyclic amines (e.g., trimethylamine, triethylamine, diisopropylamine, tributylamine), cyclic amines (e.g., N-methylmorpholine), inorganic base (e.g., sodium hydroxide, sodium hydrogen carbonate, soda ash, and potassium carbonate), and aromatic amines (e.g., dimethylaniline, dimethylaminopyridine and pyridine). According to an exemplary embodiment, the reaction is carried out in the presence of an organic base, preferably triethylamine.

According to some embodiments, the reaction of steps (a) and (c) is carried out in an organic solvent selected from a chlorinated solvent (e.g., dichloromethane); a ketone (e.g., acetone), an ester (e.g., ethyl acetate), an ether (e.g., THF), an amide (e.g., dimethylformamide or dimethylacetamide), and other solvents such as acetonitrile or toluene or mixtures thereof. According to an exemplary embodiment, the organic solvent is a chlorinated solvent, preferably dichloromethane.

Step (b) and Step (d)

According to some currently preferred embodiments, the oxidation of compounds VI and VIII is performed by a reagent selected from the group consisting of: SO$_3$-pyridine complex in the presence of triethylamine and/or DMSO, acetyl chloride or anhydride and DMSO, trifluoroacetyl chloride or anhydride and DMSO, methanesulfonyl chloride and DMSO or tetrahydro thiophene-S-oxide, toluenesulfonyl bromide and DMSO, trifluoro-methanesulfonyl anhydride (triflic anhydride) and DMSO, phosphorus pentachloride and DMSO, dimethylphosphoryl chloride and DMSO, isobutyl chloroformate and DMSO, manganese dioxide, copper oxide, dimethyl sulphoxide activated with oxalyl chloride (N. Cohen et al, J. Am. Chem. Soc., 1983, 105, 3661) or dicyclohexylcarbodiimide (R. M. Wengler, Angew. Chim. Int. Ed. Eng., 1985, 24(2), 77), or oxidation with tetrapropylammonium perruthenate (Ley et al, J. Chem. Soc. Chem. Commun., 1987, 1625), 2,2,6,6-tetramethyl-1-piperidinyloxy free radical, and an oxidizing agent such as sodium hypochlorite. According to a currently preferred embodiment, the oxidation of compounds VI and VIII is performed by SO$_3$-pyridine complex in the presence of triethylamine and DMSO. Other tertiary bases such as diisopropylethylamine, N-methylmorpholine can be used instead of triethylamine.

According to some embodiments, the reaction of steps (b) and (d) is preferably carried out at a temperature range of −10° C. and 20° C.; preferably between −5° C. and 15° C.; most preferably between 0° C. and 10° C.

According to some embodiments, the reaction of steps (b) and (d) is carried out in DMSO or mixture DMSO with an organic co-solvent selected from a chlorinated solvent (e.g., dichloromethane), a ketone (e.g., acetone), an ester (e.g., ethyl acetate), an ether (e.g., THF), an amide (e.g., dimethylformamide or dimethylacetamide), and other solvents such as acetonitrile or toluene or mixtures thereof. According to an exemplary embodiment, the organic co-solvent is toluene.

Step (e)

According to some embodiments, the stereoselective aldol condensation is performed in the presence of a chiral catalyst. According to some embodiments, the chiral catalyst is selected, yet not limited to chiral amino acids and their derivatives, for example, organic and inorganic salts, complexes with metals or peptides. According to one embodiment, the chiral catalyst is a valine. According to another embodiment, the chiral catalyst is a dipeptide. According to yet another embodiment, the chiral catalyst is other than proline. According to yet another embodiment, the chiral catalyst is chiral cyclic secondary amine, preferably, proline or 5,5-dimethyl thiazolidinium-4-carboxylic acid. According to a further embodiment, the chiral catalyst may be any chiral catalyst known in the art, such as

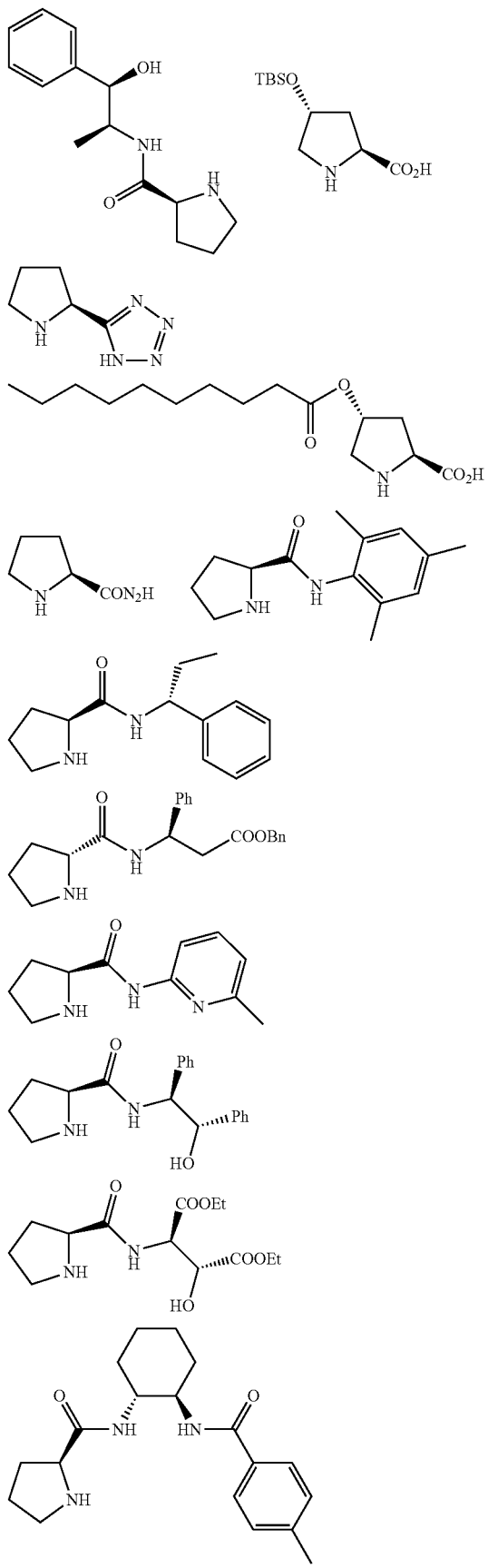

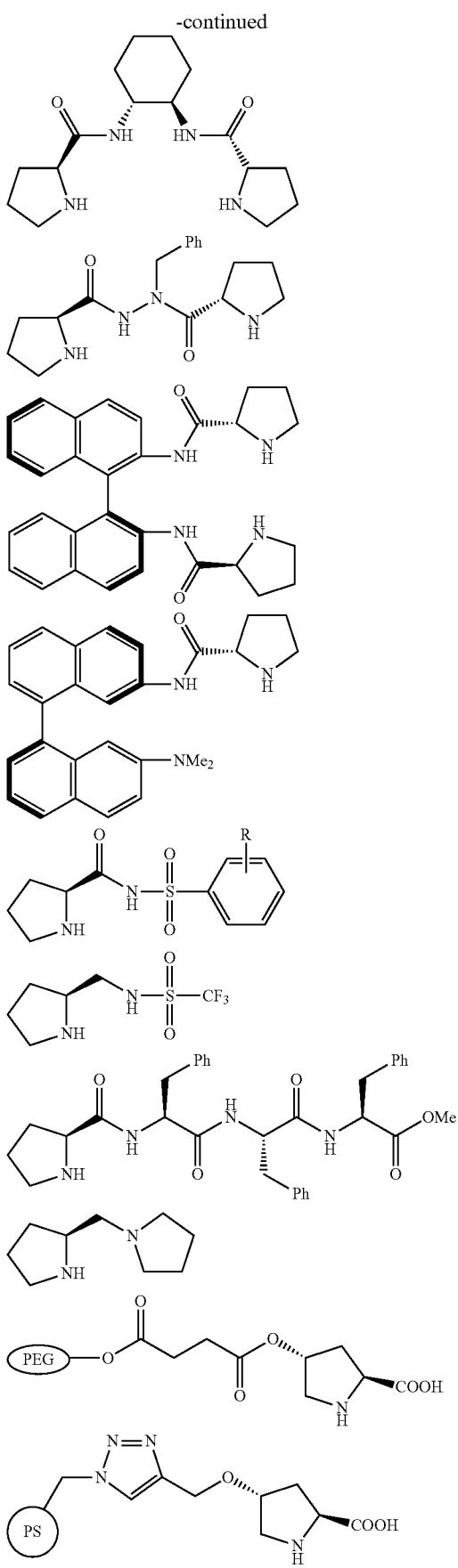
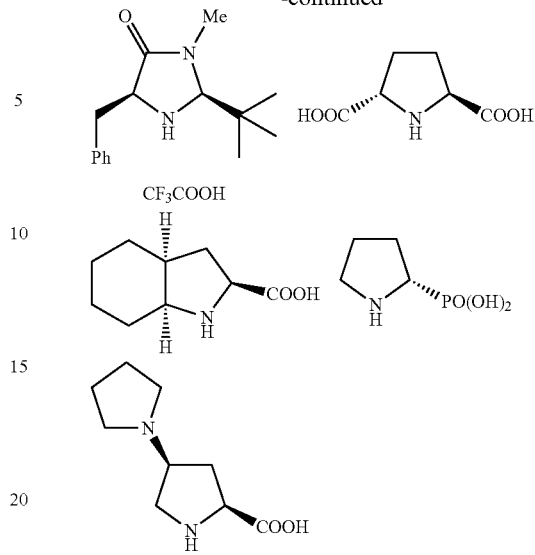

According to some embodiments, the reaction of step (e) is preferably carried out at a temperature range of about 0° C. to about 10° C.; preferably at a temperature of about 4° C.

The compound of formula VII is preferably present as about 1 to about 3 equivalents of the compound of formula IX, and more preferably as 2 equivalents of the compound of formula IX. Alternatively the compound of formula IX may be present in molar excess over the compound of formula VII.

According to some embodiments, the reaction of steps (b) and (d) is carried out in an organic solvent, preferably an amide such as dimethylformamide or dimethylacetamide.

The chiral catalyst is preferably present as about 0.05 to about 0.5 equivalents of the compound of formula IX, more preferably as 0.05 to 0.2 equivalents, yet more preferably as 0.1 equivalent. Alternatively, when the compound of formula IX is in molar excess over the compound of formula VII, then the chiral catalyst is preferably present as about 0.05 to about 0.5 equivalents of the of the compounds of formula VII, more preferably as about 0.05 to about 0.2 equivalents, yet more preferably as 0.1 equivalent.

Step (f)

According to some embodiments, the removal of the stereodirecting moieties ($Y^1$ and $Y^2$) from the product of the stereoselective aldol condensation is performed under basic conditions; alternatively under mild basic conditions; alternatively under neutral conditions. According to currently preferred embodiments, the stereodirecting moieties may be removed under basic conditions by 1,8-Diazabicycloundec-7-ene (DBU) or by a fluoride anion such as tetrabutylammonium fluoride or pyridine hydrogen fluoride. Other suitable bases may include, but are not limited to inorganic bases such as alkali metal, alkali earth metal, and ammonium hydroxides and alkoxides. Examples of suitable bases are lithium diisopropyl amide, sodium methoxide, potassium methoxide, lithium methoxide, potassium t-butoxide, calcium dihydroxide, barium dihydroxide, and quaternary alkylammonium hydroxides, DBN (1,3-diazabicyclo[3.4.0]non-5-ene), DABCO (1,4-diazabicyclo[2.2.2]octane), TBAF, TMG, potassium carbonate and sodium carbonate or mixtures thereof. According to another embodiment, the removal of the stereodirecting moieties may be performed under conditions well known in the art.

One advantage of the process of the present invention is that the removal of the $Y^1$ and $Y^2$ groups under neutral and basic conditions allows for the purification of the hydroxyaldehyde intermediate before cyclization. When using protective groups which can be removed only under acidic conditions, such intermediate purification is not possible as cyclization spontaneously occurs under acidic conditions.

The cyclization of the $Y^1$ and $Y^2$ eliminated product to obtain (3R,3aS,6aR)-hexahydrofuro[2,3-b]furan-3-ol is carried out in the presence of an acid catalyst. Non-limiting examples of acid catalysts include Lewis acids such as zinc chloride, aluminium chloride, titanium tetrachloride and the like, inorganic acids, such as hydrochloric acid, hydrofluoric acid, sulfuric acid, tungstic acid, organic acids, such as methanesulfonic acid, p-toluenesulfonic acid, and solid acids, such as acidic ion exchange resins or zeolites.

In one embodiment, the solid acids may be metal oxide systems in gel form (solid/gel systems), for example $SiO_2$, $GeO_2$, $B_2O_3$, $Al_2O_3$, $TiO_2$, $ZrO_2$ and combinations thereof. According to some embodiments, such solid/gel systems may be further treated with an acid, preferably a dibasic acid or tribasic acid, such as, for example, $H_2SO_4$, $H_3PO_4$ or orthophosphoric acid.

Other suitable acid catalysts are, for example, HBr, HI, $HClO_4$, $HBF_4$, $HPF_6$, $HAsF_6$, $HSbCl_6$, $HSbF_6$ and $HBPh_4$, aliphatic and aromatic optionally halogenated (fluorinated or chlorinated) carboxylic acids, sulfonic acids and phosphorus (V) acids (e.g., phosphonic acids or phosphonous acids), formic acid, acetic acid, propionic acid, butyric acid, benzoic acid, phenylacetic acid, cyclohexanecarboxylic acid, mono-, di- and tri-chloroacetic acid, mono-, di- and tri-fluoroacetic acid, chlorobenzoic acid, methanesulfonic acid, ethanesulfonic acid, benzenesulfonic acid, p-toluenesulfonic acid, chlorobenzenesulfonic acid, trifluoromethanesulfonic acid, methylphosphonic acid and phenylphosphonic acid.

In a further embodiment, the solid acids may be inorganic or organic ion exchangers that have been treated with a dibasic acid or tribasic acid, such as, for example, $H_2SO_4$, $H_2S_2O_7$ or $H_3PO_4$. According to one embodiment, the organic ion exchangers are polymers having acidic groups, such as for example —C(O)OH, —$SO_3H$ or —$PO_3H$ (e.g., Nafion), some of which are commercially available. According to another embodiment, the inorganic ion exchangers are natural and synthetic aluminosilicates (e.g. zeolites), some of which are commercially available (e.g., Zeolith ZSM-5, Zeolith Y and mordenite).

According to another embodiment, the solid acids are natural or synthetic silicate-like minerals that have no or only limited ion exchanging properties. Examples are phyllosilicates and argillaceous earths, for example montmorillonite, hectorite, vermiculite, kaolinite and illite. The silicates and argillaceous earths may additionally be impregnated with an acid, preferably a dibasic acid or a tribasic acid, such as, for example, $H_2SO_4$, $H_2S_2O_7$ and $H_3PO_4$. Other suitable acids have been mentioned above. In a further embodiment, the solid acids may be heteropoly acids which preferably comprise the elements Mo, V, W, O and H. These heteropoly acids may further comprise B, Si or P as well as secondary or trace elements and may have the following general formulae:

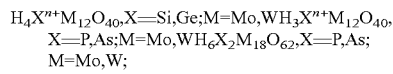

for example, phosphotungstic acid, tungstosilicic acid and molybdophosphoric acid.

According to some embodiments, the steps (a-f) can be combined and carried out in a single step without the need to separate intermediate compounds. Alternatively, some, but not all, of the steps (a-f) are combined and carried out in a single step.

EXAMPLES

Example 1a

Preparation of (3R,3aS,6aR)-hexahydrofuro[2,3-b]furan-3-yl-N-[(1S,2R)-3-chloro-1-benzyl-2-hydroxypropyl]carbamate (Compound IV)

1,1'-carbonyldiimidazole (162.15 g, 1 mol) was added to THF (0.5 L), following by solution of (3R,3aS,6aR)-hexahydrofuro[2,3-b]furan-3-ol (135.2 g, 1.04 mol) in 0.3 L of THF and the mixture was stirred for a further hour. (2S,3S)-3-amino-1-chloro-2-hydroxy-4-phenylbutane hydrochloride (229 g, 0.97 mol) was added and the mixture heated at 55-60° C. approximately 5-6 hours under TLC control (for complete disappearance of (2S,3S)-3-amino-1-chloro-2-hydroxy-4-phenylbutane). After completion of reaction the solution was cooled and transformed to the next step. For the preparation of analytical sample, 10 ml of solution was diluted with 50 ml of ethyl acetate, washed with water (40 mL), diluted hydrochloric acid (40 ml), 5% aqueous sodium hydrogen carbonate (40 mL) and water (50 mL). The solution was dried over sodium sulfate and evaporated to dryness. MS: m/z 356 (MH+). NMR spectrum corresponded to the structure of the desired product.

Example 1b

Preparation of (3R,3aS,6aR)-hexahydrofuro[2,3-b]furan-3-yl-N-[(1S,2R)-3-chloro-1-benzyl-2-hydroxypropyl]carbamate (Compound IV)

1. (3R,3aS,6aR)-hexahydrofuro[2,3-b]furan-3-ol (100 mg) was added into a pre-dried 25 ml round bottom flask under nitrogen. Disuccinimidyl carbonate (DSC) (295 mg) was then added followed by acetonitrile (3 ml). $Et_3N$ (155 mg) was added while stirring, until the suspension became clear. The resulting solution was stirred at ambient temperature for 5 hours under TLC control. The solvent was then removed, saturated solution of $NaHCO_3$ (4 ml) was added, and extracted with EtOAc (3*20 ml). The combined organic fractions were dried with $Na_2SO_4$, filtered, and concentrated to an oily residue. MeOH (4 ml) was added, and the resulting suspension was stirred, then filtered and dried to give 152 mg of compound III as a white solid.
2. Compound III from above (125 mg) was added into a pre-dried 25 ml round bottom flask under nitrogen. (2S,3S)-3-amino-1-chloro-2-hydroxy-4-phenylbutane hydrochloride (94 mg), $Et_3N$ (0.4 ml), and $CH_2Cl_2$ (20 ml) were added and stirred at ambient temperature for 3 hours, under TLC control. The solvent was then filtered, the organic layer was washed with 5% $NaH_2PO_4$ (5 ml) and with water (15 ml), then dried over $Na_2SO_4$, filtered and concentrated to give 120 mg of compound 5 as a white solid. NMR spectrum corresponded to structure.

Example 2

Preparation of (3R,3aS,6aR)-hexahydrofuro[2,3-b]furan-3-yl-N-[(1S,2R)-3-isobutylamino-1-benzyl-2-hydroxypropyl]carbamate (Compound V)

1. A mixture from previous step, isobutylamine 73.8 g (1.01 mol) and sodium hydrogen carbonate (92.4, 1.1 mol) in water (1 L) was heated at a gentle reflux (~60° C.) with stirring until reaction completed under TLC control (~5 h). Excess isobutyl amine and THF were removed by distillation under nitrogen at an internal reaction temperature of 70-75° C. Additional water (500 g) was added and the product was isolated by filtration, washed with water and dried in vacuum, yielded 360 g (92%) of white to off-white solid, MS: m/z 393 (MH$^+$), 427 [M+Cl]$^-$, NMR spectrum corresponded to structure.

2. Compound IV (100 mg) and isobutylamine (2 ml) were added into a pre-dried 10 ml round bottom flask. The reaction was heated to 60° C. overnight under TLC control. The excess isobutylamine was evaporated and the residue was subjected to column chromatography (eluent: MeOH: CH$_2$Cl$_2$, 1:10) to give 80 mg of the product. MS: m/z 393 (MH$^+$), 427 [M+Cl]$^-$, NMR spectrum corresponded to structure.

Example 3

Preparation of (3R,3aS,6aR)-hexahydrofuro[2,3-b] furan-3-yl (1S, 2R)-3-[[(4-aminophenyl)sulfonyl] (isobutyl)amino]-1-benzyl-2-hydroxypropyl carbamate ethanoate (Compound I) (Darunavir, Also Designated [(1S,2R)-3-[[(4-aminophenyl)sulfonyl](2-methylpropyl)amino]-2-hydroxy-1-(phenylmethyl) propyl]-carbamic acid (3R,3aS,6aR)hexahydrofuro [2,3-b]furan-3-yl ester)

(1-Benzyl-2-hydroxy-3-isobutylamino-propyl)-carbamic acid hexahydro-furo[2,3-b]-furan-3-yl ester (98.1 g, 0.25 mol, 1 equiv) was dissolved in dichloromethane (200 mL), followed by the addition of saturated NaHCO$_3$ solution (300 ml). P-aminophenylsulfonyl chloride (48.8 g, 0.255 mol, 1.02 equiv) (58.1 g for p-aminophenylsulfonyl chloride hydrochloride) was added in portions to the previous solution. The solution was vigorously stirred at 20-35° C. under TLC control. After completion of the reaction (~4 h), the organic layer was separated and washed with saturated NaHCO$_3$ solution (100 ml), water (100 ml), 5% HCl solution (100 ml) and brine (100 ml). The organic layer was dried on Na$_2$SO$_4$, filtered, and ethanol was added. Methylene chloride was distilled off. The temperature was kept around 40-45° C. and crystallization was initiated by seeding. The mixture was cooled, stirred for another 2-3 h. The precipitate was filtered and washed with cold ethanol. The wet product was dried in vacuo at 40° C. to give 136.5 g (92%) of (3R,3αS,6αR)-hexahydrofuro[2,3-b]furan-3-yl (1S,2R)-3-[[(4-aminophenyl)sulfonyl] (isobutyl)amino]-1-benzyl-2-hydroxypropyl carbamate ethanoate with the purity >98.5%.

Example 4

Preparation of (3R,3aS,6aR)-hexahydrofuro[2,3-b] furan-3-yl (1S, 2R)-3-[[(4-aminophenyl)sulfonyl] (isobutyl)amino]-1-benzyl-2-hydroxypropyl carbamate ethanoate (Compound I by a Single Step Synthesis)

1,1'-carbonyldiimidazole (162.15 g, 1 mol) was added to THF (0.5 L), following by solution of (3R,3aS,6aR)-hexahydrofuro[2,3-b]furan-3-ol (135.2 g, 1.04 mol) in 0.3 L of THF and the mixture was stirred for a further hour. (2S,3S)-3-amino-1-chloro-2-hydroxy-4-phenylbutane hydrochloride (229 g, 0.97 mol) was added and the mixture heated at 55-60° C. approximately 5-6 hours under TLC control (for complete disappearance of (2S,3S)-3-amino-1-chloro-2-hydroxy-4-phenylbutane). After completion of reaction the solution was cooled to room temperature and isobutylamine 73.8 g (1.01 mol) and sodium hydrogen carbonate (92.4 g, 1.1 mol) in water (1 L) were added. The mixture was heated at a gentle reflux (~60° C.) with stirring until reaction completed under TLC control (~5 h). The mixture was cooled to room temperature and 100 g (1.2 mol) of sodium bicarbonate was added, following by p-aminophenylsulfonyl chloride (48.8 g, 0.255 mol, 1.02 equiv). The solution was vigorously stirred at 40-45° C. under TLC control. After completion of the reaction (~3-4 h), the solvents were distilled at 40-45° C. under reduced pressure to half of overall volume, the resulted slurry was stirred 1 h at room temperature and 2 h at 10° C. Filtered, washed with water and dried in vacuum. The yield of crude product is 88%, purity—92%. The crude compound was crystallized from ethanol.

Example 5

Preparation of Alcohol Mono Substituted by the Stereodirecting Group Fmoc (Compounds VI and VIII)

To a stirred solution of 665 mmol (60 g of 1,4-butanediol or 41 g of 1,2-ethanediol) and 25 g (248 mmol) triethylamine in 300 g dichloromethane a solution of 57.7 g (223 mmol) fluorenylmethyloxycarbonyl chloride (Fmoc-Cl) in 30 g dichloromethane was added dropwise over 45 min at ambient temperature. The solution was stirred for about 1 h followed by the addition of 250 g saturated aq. sodium bicarbonate. The organic layer was then washed with 250 ml water, dried (Na$_2$SO$_4$) and concentrated under vacuum. The obtained product may be used without further purification in the next step or it may be purified by crystallization or by flash chromatography giving the mono-protected alcohol in >95% purity and 83-92% yield (calculated based on Fmoc-Cl).

Example 6

Preparation of Compounds Having the Structures VII and IX Wherein Y$^1$ and Y$^2$ are Fmoc Moiety)

To a cooled (−5° C.) solution of 28 g of 1,4-butanediol mono-substituted with Fmoc (88 mmol) in 100 mL toluene and 37 g (366 mmol) triethylamine, a solution of SO$_3$-pyridine complex (39 g, 245 mmol) in DMSO (175 g) was added during 1 h with the temperature being kept between 0° C. and 10° C. After stirring for 30 min, TLC analysis showed complete conversion. Water (100 mL) was added and after 10 min stirring the aqueous layer was extracted with 100 mL toluene. The combined toluene layers were washed with 150 mL water and concentrated to 41 g of a residue. Crystallization of this residue yielded 18 g of 4-Fmoc-n-butyraldehyde (99% pure by GC) corresponding to a yield of 75% based on the mono-protected alcohol.

Example 7

Preparation of (3R,3aS,6aR)-hexahydrofuro[2,3-b]furan-3-ol a) A solution of Fmoc-acetaldehyde (2.0 mmol, 2 equiv) in DMF (500 mL) was added slowly over the course of 2.5 h to a stirring mixture of Fmoc-n-butyraldehyde (1.0 mmol, 1 equiv) and (S)-proline (0.10 mmol, 0.1 equiv) in DMF (500 mL) at 4° C. The resulting mixture was stirred for 16 h at the same temperature. The reaction progress was monitored by TLC. When the reaction was terminated, a catalytic amount of DBU was added and the mixture was stirred at 1-2 h under TLC control. Upon reaction termination (removal of the Fmoc group), a brown-colored reaction mixture was obtained. The product was then filtered, and the filtrate was evaporated under high vacuum at 22-30° C. (bath temperature). The residue was dissolved in water (0.5 L) and extracted with toluene or hexane.

b) To the aqueous solution from step (a) 300 g of 3-5% wt aq. HCl were added at 2-5° C. Stirring was continued for additional 20 h, then 38 g of pyridine, 2000 g toluene and 650 ml water were added. After additional 1 h stirring, the mixture was filtered over a decalite pre-coated filter. The toluene layer was extracted with 4×600 ml water and the combined aqueous phase was washed with 1200 g toluene. The aqueous phase was then concentrated under vacuum to about 850 ml, which were then extracted with ethyl acetate six times, each time with 1500 ml; the combined organic layer was washed with 450 ml water, 400 ml 5% HCl and 500 ml of 5% sodium carbonate and then dried with 1000 g $Na_2SO_4$. The organic layer (ethyl acetate) was concentrated under vacuum, and 160.2 g of brown oil were obtained, corresponding to a yield of 85% based on the mono-protected butyraldehyde, with enantiomeric purity of >95%. The required product was further purified by Flash chromatography.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

What is claimed is:

1. A process for the preparation of the compound of formula (I):

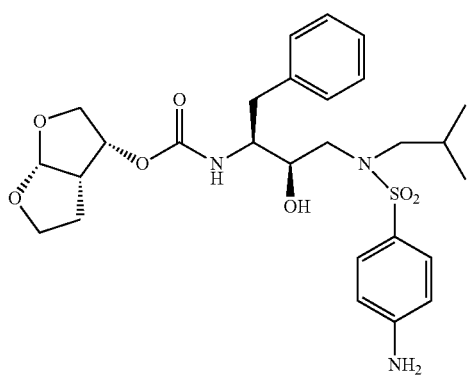

(I)

comprising the steps of:

i) reacting a 3-amino-2-hydroxy-4-phenylbutane derivative of formula (II)

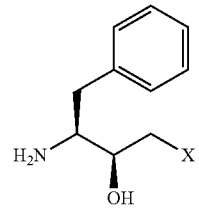

(II)

wherein X is a leaving group selected from the group consisting of a halogen, sulfonate, alkanoate and —$N^+Me_3X'^-$, wherein X' is —OTf, —OTs, —I, —Br, —Cl or —OH, with a (3R, 3aS, 6aR)-hexahydrofuro [2,3-b] furan-3-yloxy carbonyl derivative of formula (III)

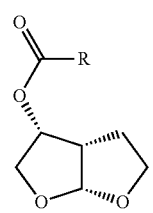

(III)

wherein R is selected from the group consisting of halogen, imidazolyl, benzotriazolyl, oxysuccinimidyl, oxybenzotriazolyl, 4-nitrophenoxy, 4-methoxyphenoxy, 2-nitrophenoxy and pentafluorophenoxy to obtain a compound of formula (IV);

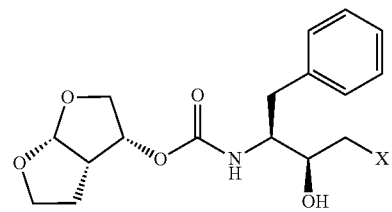

(IV)

ii) reacting the compound of formula (IV) with isobutylamine to obtain a compound of formula (V)

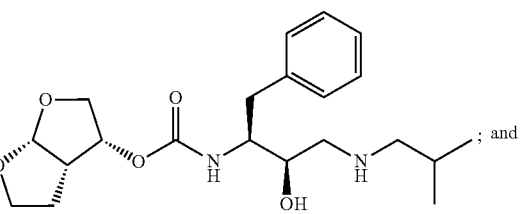

(V)

; and iii) reacting the compound of formula (V) with a substituted phenylsulfonyl derivative to form a compound of formula (I).

2. The process of claim 1, wherein X is selected from the group consisting of Cl, Br, I, MsO and TsO.

3. The process of claim 1, wherein the 3-amino-2-hydroxy-4-phenylbutane derivative of formula (II) is (2S, 3S)-3-amino-1-chloro-2-hydroxy-4-phenylbutane.

4. The process of claim 1, wherein the (3R, 3aS, 6aR)-hexahydrofuro [2, 3-b] furan-3-yloxy carbonyl derivative of formula (III) is (3R, 3aS, 6aR)-hexahydrofuro [2, 3-b] furan-3-yl imidazolyl carbonate, which is obtained by reacting (3R, 3aS, 6aR)-hexahydrofuro [2,3-b] furan-3-ol with 1,1'-carbonyldiimidazole.

5. The process of claim 4, wherein the reaction of (3R, 3aS, 6aR)-hexahydrofuro [2, 3-b] furan-3-ol with 1,1'-carbonyldiimidazole to obtain the compound of formula (III), followed by reaction of compound (III) with the compound of formula (II) is carried out in a single step.

6. The process of claim 1, wherein the (3R, 3aS, 6aR)-hexahydrofuro [2, 3-b] furan-3-yloxy carbonyl derivative of formula (III) is (3R, 3aS, 6aR)-hexahydrofuro [2, 3-b] furan-3-yl oxysuccinimide carbonate, which is obtained by reacting (3R, 3aS, 6aR)-hexahydrofuro [2,3-b] furan-3-ol with disuccinimidyl carbonate (DSC).

7. The process of claim 6, wherein the reaction of (3R, 3aS, 6aR)-hexahydrofuro [2, 3-b] furan-3-ol with disuccinimidyl carbonate to obtain the compound of formula (III), followed by reaction of compound (III) with the compound of formula (II) is carried out in a single step.

8. The process of claim 1, wherein the compound of formula (II) is in a form of salt.

9. The process of claim 1, wherein the substituted phenylsulfonyl derivative in step (iii) is a p-aminophenylsulfonyl halide.

10. The process of claim 1, wherein steps (i) and (ii) are carried out in a single step, or wherein steps (i)-(iii) are carried out in a single step.

11. The process of claim 1, wherein the compound of formula (III) is prepared by reacting (3R, 3aS, 6aR)-hexahydrofuro [2,3-b] furan-3-ol with a coupling agent of formula RCO-Y wherein Y is a leaving group selected from the group consisting of a halogen, sulfonate, alkanoate and —N⁺Me₃X'⁻, wherein X' is —OTf —OTs —I —Br, —Cl or —OH and R is as defined in claim 1.

12. The process of claim 11, wherein the (3R, 3aS, 6aR)-hexahydrofuro [2, 3-b] furan-3-ol is obtained by a process comprising the steps of:
(a) reacting an ethanol derivative of the general formula HO—CH₂—CH₂—X¹, with a reagent comprising a stereodirecting moiety (Y¹) to obtain a compound having the formula (VI):

HO—CH₂—CH₂—OY¹    VI wherein X¹ is OH or a leaving group selected from the group consisting of a halogen, sulfonate, alkanoate and —N⁺Me₃X'⁻, wherein X' is —OTf, —OTs, —I, —Br, —Cl or —OH and the stereodirecting moiety Y¹ is removable under neutral or basic conditions;
(b) oxidizing compound (VI) to obtain an aldehyde having the formula (VII);

O=CH—CH₂—OY¹    VII (c) reacting a butanol derivative of the general formula HO—(CH₂)₄—X², with a reagent comprising a stereodirecting moiety (Y²) to obtain a compound having the formula (VIII);

HO—(CH₂)₄—OY²    VIII wherein X² is OH or a leaving group selected from the group consisting of a halogen, sulfonate, alkanoate and —N⁺Me₃X'⁻, wherein X' is —OTf, —OTs, —I, —Br, —Cl or —OH, and the stereodirecting moiety Y² is removable under neutral or basic conditions;

wherein the stereodirecting moieties Y¹ and Y² are each independently selected from the group consisting of fluorenylmethyloxycarbonyl (Fmoc), p-nitrobenzenesulfoethoxycarbonyl, propargyloxycarbonyl, picolinyl, prenyl, o-nitrobenzyloxy methyl, 4-methyoxyphenoxymethyl, guaiacolmethyl, siloxymethyl, 2-cyanoethyoxymethyl, 2-quinolinylmethyl, dichloroacetyl, trichloroacetyl and 2-[4-nitrophen]ethylsufonate;
(d) oxidizing compound (VIII) to obtain an aldehyde having the formula (IX)

O=CH—(CH₂)₃—OY²    IX;

(e) stereoselectively coupling compounds (VII) and (IX) by aldol condensation in the presence of a chiral catalyst to form a compound of formula (X)

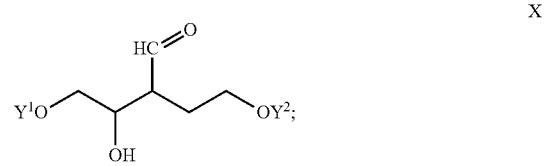

and
(f) removing the stereodirecting moieties (Y¹ and Y²) from the product of step (e) followed by cyclization in the presence of an acid catalyst to form (3R,3aS,6aR)-hexahydrofuro [2,3-b] furan-3-ol.

13. The process of claim 12, wherein X¹ and X² are each OH.

14. The process of claim 12, wherein Y¹ and Y² are each fluorenylmethyloxycarbonyl (Fmoc).

15. The process of claim 12, wherein step (f) comprises removing the groups Y¹ and Y² under basic or neutral conditions.

16. The process of claim 12, wherein step (f) comprises removing the groups Y¹ and Y² with DBU or with fluoride (F—).

17. The process of claim 12, wherein the chiral catalyst is selected from the group consisting of proline, valine 5,5-dimethyl thiazolidinium-4-carboxylic acid,

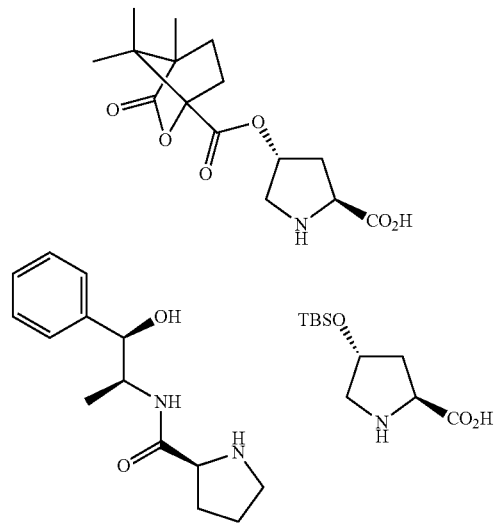

-continued
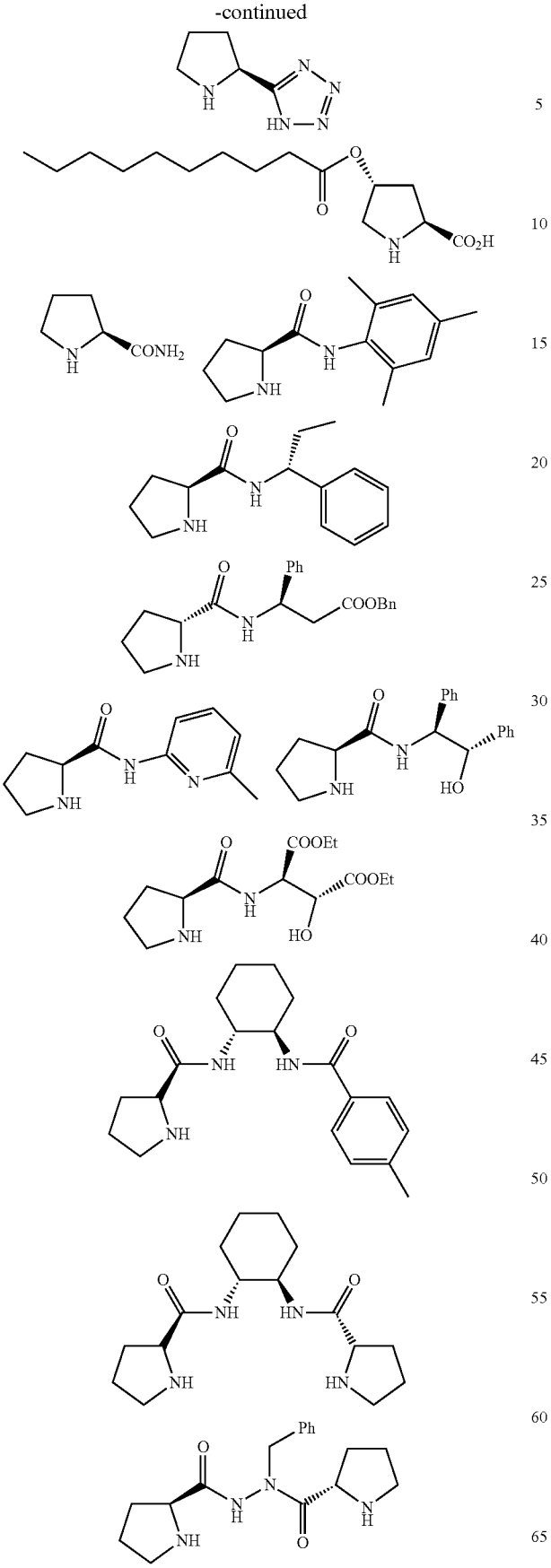
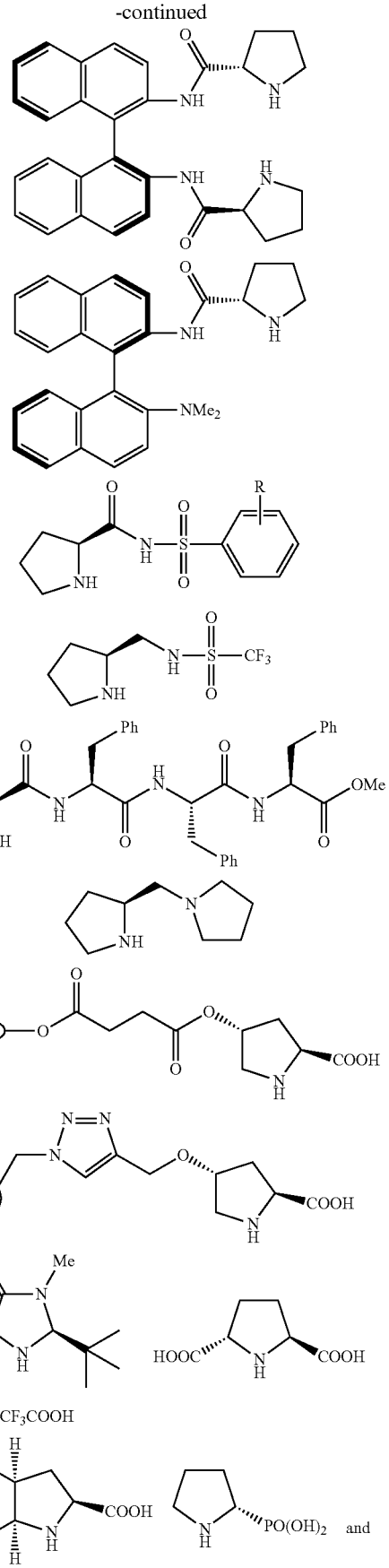

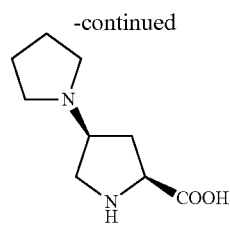

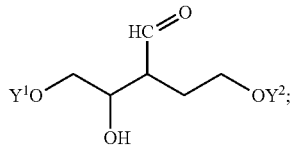

18. The process of claim 17, wherein the chiral catalyst is proline.

19. The compound (3R, 3aS, 6aR)-hexahydrofuro [2,3-b] furan-3-yl —N-[(1 S, 2R)-3-chloro-1-benzyl-2-hydroxypropyl] carbamate, produced by the process of claim 1.

20. A process for the preparation of (3R,3aS,6aR)-hexahydrofuro [2,3-b] furan-3-ol comprising the steps of:
(a) reacting an ethanol derivative of the general formula HO—CH2—CH$_2$—X$^1$ with a reagent comprising a stereodirecting moiety (Y$^1$) to obtain a compound having the formula (VI):

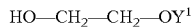

HO—CH$_2$—CH$_2$—OY$^1$     VI wherein X$^1$ is OH or a leaving group selected from the group consisting of a halogen, sulfonate, alkanoate and —N$^+$Me$_3$X'$^-$, wherein X' is —OTf, —OTs, —I, —Br, —Cl or —OH and the stereodirecting moiety Y$^1$ is removable under neutral or basic conditions;

(b) oxidizing compound (VI) to obtain an aldehyde having the formula (VII)

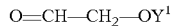

O=CH—CH$_2$—OY$^1$     VII (c) reacting a butanol derivative of the general formula HO—(CH$_2$)$_4$—X$^2$ with a reagent comprising a stereodirecting moiety (Y$^2$) to obtain a compound having the formula (VIII)

HO—(CH$_2$)$_4$—OY$^2$     VIII wherein X$^2$ is OH or a leaving group selected from the group consisting of a halogen, sulfonate, alkanoate and —N$^+$Me$_3$X'$^-$, wherein X' is —OTf, —OTs, —I, —Br, —Cl or —OH, and the stereodirecting moiety Y$^2$ is removable under neutral or basic conditions;

wherein the stereodirecting moieties Y$^1$ and Y$^2$ are each independently selected from the group consisting of fluorenylmethyloxycarbonyl (Fmoc), p-nitrobenzenesulfoethoxycarbonyl, propargyloxycarbonyl, picolinyl, prenyl, o-nitrobenzyloxy methyl, 4-methyoxyphenoxymethyl, guaiacolmethyl, siloxymethyl, 2-cyanoethyoxymethyl, 2-quinolinylmethyl, dichloroacetyl, trichloroacetyl and 2-[4-nitrophenyl]ethylsulfonate;

(d) oxidizing compound (VIII) to obtain an aldehyde having the formula (IX)

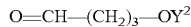

O=CH—(CH$_2$)$_3$—OY$^2$     IX (e) stereoselectively coupling compounds (VII) and (IX) by aldol condensation in the presence of a chiral catalyst to form a compound of formula (X)

and
(f) removing the stereodirecting moieties (Y$^1$ and Y$^2$) from the product of step (e) followed by cyclization in the presence of an acid catalyst to form (3R,3aS,6aR)-hexahydrofuro [2,3-b] furan-3-ol.

21. The process of claim 20, further comprising the step of reacting (3R,3aS,6aR)-hexahydrofuro [2,3-b] furan 3ol with a coupling agent of formula RCO—Y wherein Y is a leaving group selected from the group consisting of a halogen, sulfonate, alkanoate and —N$^+$Me$_3$X'$^-$, wherein X' is —OTf —OTs, —I, —Br, —Cl or —OH, and R is selected from the group consisting of halogen, imidazolyl, benzotriazolyl, oxysuccinimidyl, oxybenzotriazolyl, 4-nitrophenoxy, 4-methoxyphenoxy, 2-nitrophenoxy and pentafluorophenoxy, to obtain a (3R, 3aS, 6aR)-hexahydrofuro [2,3-b1 ]furan-3-yloxy carbonyl derivative of formula (III)

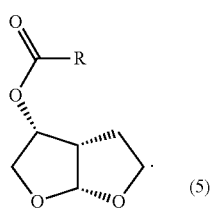

22. A compound represented by the general formula HO—(CH$_2$)$_n$—OY or O=CH—(CH$_2$)$_3$—OY, wherein Y is a stereodirecting moiety which can be removed under neutral or basic conditions, selected from the group consisting of fluorenylmethyloxycarbonyl (Fmoc), p-nitrobenzenesulfoethoxycarbonyl, propargyloxycarbonyl, picolinyl, prenyl, o-nitrobenzyloxy methyl, 4-methyoxyphenoxymethyl, guaiacolmethyl, siloxymethyl, 2-cyanoethyoxymethyl, 2-quinolinylmethyl, dichloroacetyl, trichloroacetyl and 2-[4-nitrophenyl]ethylsulfonate; and n is 2 or 4.

23. The compound of claim 22, wherein Y is fluorenylmethyloxycarbonyl (Fmoc).

24. The process of claim 1, wherein X is a sulfonate selected from the group consisting of —OSO$_2$(C$_n$H$_{2n+1}$) wherein n=0-4; and —OSO$_2$—R$^P$, where R$^P$ is an optionally substituted phenyl group; or wherein X is selected from the group consisting of a halogen, alkanoate and —N$^+$Me$_3$X'$^-$, wherein X' is —OTf, —OTs, —I, —Br, —Cl or —OH.

25. The process of claim 20, wherein X$^1$ and X$^2$ are each independently a sulfonate selected from the group consisting of —OSO$_2$(C$_n$H$_{2n+1}$) wherein n=0-4; and —OSO$_2$—R$^P$, where R$^P$ is an optionally substituted phenyl group; or wherein X$^1$ and X$^2$ are each independently selected from the group consisting of a halogen, alkanoate and —N$^+$Me$_3$X'$^-$, wherein X' is —OTf, —OTs, —I, —Br, —Cl or —OH.

* * * * *